US012758343B2

(12) United States Patent
Lu et al.

(10) Patent No.: US 12,758,343 B2
(45) Date of Patent: Oct. 13, 2026

(54) MASTER MANIPULATORS OF ROBOTS

(71) Applicant: WUHAN UNITED IMAGING SURGICAL CO., LTD., Wuhan (CN)

(72) Inventors: Zhuangzhuang Lu, Wuhan (CN); Ting Ye, Wuhan (CN); Saili Wang, Wuhan (CN)

(73) Assignee: WUHAN UNITED IMAGING SURGICAL CO., LTD., Wuhan (CN)

( * ) Notice: Subject to any disclaimer, the term of this patent is extended or adjusted under 35 U.S.C. 154(b) by 206 days.

(21) Appl. No.: 18/363,687

(22) Filed: Aug. 1, 2023

(65) Prior Publication Data

US 2023/0372044 A1 Nov. 23, 2023

Related U.S. Application Data

(63) Continuation of application No. PCT/CN2022/075245, filed on Jan. 30, 2022.

(30) Foreign Application Priority Data

Feb. 1, 2021 (CN) ......................... 202110135533.0
Apr. 26, 2021 (CN) ......................... 202110454129.X
Apr. 26, 2021 (CN) ......................... 202110454699.9

(51) Int. Cl.
*A61B 34/00* (2016.01)
*A61B 17/00* (2006.01)
(Continued)

(52) U.S. Cl.
CPC .......... *A61B 34/76* (2016.02); *A61B 17/3403* (2013.01); *A61B 2017/00367* (2013.01); *A61B 2017/3405* (2013.01); *A61B 34/35* (2016.02)

(58) Field of Classification Search
CPC ...... A61B 17/3403; A61B 2017/00367; A61B 2017/3405; A61B 2017/3409; A61B 34/35; A61B 34/37; A61B 34/74; A61B 34/76
See application file for complete search history.

(56) References Cited

U.S. PATENT DOCUMENTS 4,732,353 A 3/1988 Studer
6,377,011 B1 4/2002 Ben-Ur
(Continued)

FOREIGN PATENT DOCUMENTS

CN 101261781 A 9/2008
CN 101444431 A 6/2009
(Continued)

OTHER PUBLICATIONS

First Office Action in Chinese Application No. 202110135533.0 mailed on Feb. 28, 2025, 18 pages.
(Continued)

*Primary Examiner* — Mohamed G Gabr
*Assistant Examiner* — Khoa Tan Le
(74) *Attorney, Agent, or Firm* — Poseidon Advanced IP LLC

(57) ABSTRACT

Disclosed is a master manipulator of a robot. The master manipulator may comprise a puncture component including a handle housing, a puncture actuator movably arranged on the handle housing, and a force feedback mechanism arranged at a bottom of the handle housing, the force feedback mechanism and the puncture actuator being connected, and the force feedback mechanism applying resistance to the puncture component based on puncture force feedback information; and an attitude adjustment part.

19 Claims, 16 Drawing Sheets

(51) Int. Cl.

| | |
|---|---|
| ***A61B 17/34*** | (2006.01) |
| ***A61B 34/35*** | (2016.01) |

(56) References Cited

U.S. PATENT DOCUMENTS

| | | | | |
|---|---|---|---|---|
| 6,429,849 | B1 | 8/2002 | An et al. | |
| 2002/0040217 | A1 | 4/2002 | Jinno | |
| 2004/0024311 | A1 | 2/2004 | Quaid, III | |
| 2008/0154246 | A1 | 6/2008 | Nowlin et al. | |
| 2009/0024142 | A1 | 1/2009 | Ruiz Morales | |
| 2009/0248035 | A1* | 10/2009 | Sjostedt ............ | A61M 25/0136 606/129 |
| 2012/0053701 | A1 | 3/2012 | Yi et al. | |
| 2014/0039527 | A1 | 2/2014 | Avelar et al. | |
| 2016/0059409 | A1 | 3/2016 | Nawrat et al. | |
| 2016/0374772 | A1 | 12/2016 | Hasegawa et al. | |
| 2017/0151028 | A1 | 6/2017 | Ogawa et al. | |
| 2018/0353246 | A1 | 12/2018 | Ishihara et al. | |
| 2019/0192247 | A1* | 6/2019 | Woo ........................ | A61B 34/37 |
| 2019/0350662 | A1 | 11/2019 | Huang et al. | |
| 2020/0015917 | A1 | 1/2020 | Cavalier et al. | |
| 2020/0289230 | A1 | 9/2020 | Denlinger et al. | |
| 2020/0294423 | A1 | 9/2020 | Blain et al. | |
| 2020/0356174 | A1 | 11/2020 | Andreff et al. | |

FOREIGN PATENT DOCUMENTS

| | | | |
|---|---|---|---|
| CN | 101933837 | A | 1/2011 |
| CN | 102208150 | A | 10/2011 |
| CN | 102758734 | A | 10/2012 |
| CN | 103386687 | A | 11/2013 |
| CN | 103565529 | A | 2/2014 |
| CN | 103632594 | A | 3/2014 |
| CN | 203619682 | U | 6/2014 |
| CN | 104622585 | A | 5/2015 |
| CN | 104669299 | A | 6/2015 |
| CN | 104690708 | A | 6/2015 |
| CN | 105108762 | A | 12/2015 |
| CN | 105196284 | A | 12/2015 |
| CN | 105662589 | A | 6/2016 |
| CN | 106667583 | A | 5/2017 |
| CN | 107297677 | A | 10/2017 |
| CN | 107321969 | A | 11/2017 |
| CN | 107361848 | A | 11/2017 |
| CN | 107496031 | A | 12/2017 |
| CN | 107595395 | A | 1/2018 |
| CN | 206953010 | U | 2/2018 |
| CN | 207352855 | U | 5/2018 |
| CN | 108742797 | A | 11/2018 |
| CN | 108852514 | A | 11/2018 |
| CN | 109171986 | A | 1/2019 |
| CN | 109620367 | A | 4/2019 |
| CN | 109620413 | A | 4/2019 |
| CN | 109621330 | A | 4/2019 |
| CN | 208993750 | U | 6/2019 |
| CN | 110623710 | A | 12/2019 |
| CN | 209790401 | U | 12/2019 |
| CN | 210019449 | U | 2/2020 |
| CN | 111110353 | A | 5/2020 |
| CN | 111329581 | A | 6/2020 |
| CN | 111407409 | A | 7/2020 |
| CN | 111449758 | A | 7/2020 |
| CN | 111604874 | A | 9/2020 |
| CN | 111839740 | A | 10/2020 |
| CN | 111973276 | A | 11/2020 |
| CN | 112338939 | A | 2/2021 |
| CN | 112349191 | A | 2/2021 |
| CN | 112497234 | A | 3/2021 |
| CN | 113116519 | A | 7/2021 |
| CN | 113208738 | A | 8/2021 |
| CN | 215265162 | U | 12/2021 |
| EP | 3685780 | A1 | 7/2020 |
| GB | 1263424 | A | 2/1972 |
| KR | 20100085621 | A | 7/2010 |
| KR | 20180044524 | A | 5/2018 |
| WO | 2018112227 | A2 | 6/2018 |
| WO | 2019058336 | A1 | 3/2019 |
| WO | 2020188391 | A1 | 9/2020 |
| WO | 2020218678 | A1 | 10/2020 |

OTHER PUBLICATIONS

International Search Report in PCT/CN2022/075245 mailed on May 5, 2022, 10 pages.

Written Opinion in PCT/CN2022/075245 mailed on May 5, 2022, 12 pages.

International Search Report in PCT/CN2022/075243 mailed on May 7, 2022, 8 pages.

Written Opinion in PCT/CN2022/075243 mailed on May 7, 2022, 10 pages.

International Search Report in PCT/CN2022/075244 mailed on Apr. 14, 2022, 7 pages.

Written Opinion in PCT/CN2022/075244 mailed on Apr. 14, 2022, 10 pages.

The Extended European Search Report in European Application No. 22745370.1 mailed on May 8, 2024, 7 pages.

The Extended European Search Report in European Application No. 22745368.5 mailed on May 8, 2024, 8 pages.

Partial Supplementary European Search Report in European Application No. 22745369.3 mailed on May 22, 2024, 12 pages.

The Second Office Action in Chinese Application No. 202110135533.0 mailed on Aug. 6, 2025, 22 pages.

The Second Office Action in Chinese Application No. 202211025629.2 mailed on Mar. 11, 2026, 19 pages.

* cited by examiner

MASTER MANIPULATORS OF ROBOTS

CROSS-REFERENCE TO RELATED APPLICATIONS

This application is a Continuation of International Application No. PCT/CN2022/075245, filed on Jan. 30, 2022, which claims priority of the Chinese Patent Application No. 202110135533.0, filed on Feb. 1, 2021, the Chinese Patent Application No. 202110454699.9, filed on Apr. 26, 2021, and the Chinese Patent Application No. 202110454129.X, filed on Apr. 26, 2021, the contents of each of which are hereby incorporated by reference.

TECHNICAL FIELD

The present disclosure relates to the field of puncture devices, and in particular to master manipulators of robots.

BACKGROUND

The master-slave teleoperation mode of robot-assisted puncture operation is a surgical method. By remotely controlling the image-guided puncture robot to perform the puncture operation, doctors can be effectively protected from radiation exposure. However, a master-slave teleoperated robot intelligently controls the puncture needle to move at a preset speed, which cannot simulate a puncture process performed by a doctor that holds the needle, and cannot feedback a puncture force. If the doctor lacks a force perception, it may increase the risk and uncertainty of the puncture operation, increase the operation time, reduce the efficiency of surgery, and affect the success rate of the puncture operation.

Therefore, it is desirable to provide master manipulators of robots, which can control a needle insertion operation at an end of a robotic arm and feedback the needle insertion resistance at the end of the robotic arm.

SUMMARY

One aspect of the present disclosure provides a master manipulator of a robot. The master manipulator may comprise a puncture component including a handle housing, a puncture actuator movably arranged on the handle housing, and a force feedback mechanism arranged at a bottom of the handle housing, the force feedback mechanism and the puncture actuator being connected, and the force feedback mechanism applying resistance to the puncture component based on puncture force feedback information; and an attitude adjustment part.

In some embodiments, the attitude adjustment part may include an attitude adjustment force feedback component, and the attitude adjustment force feedback component may apply resistance to the attitude adjustment part based on attitude adjustment force feedback information.

In some embodiments, the attitude adjustment part may include a plurality of attitude adjustment trigger switches, and the plurality of attitude adjustment trigger switches may be arranged along a peripheral side of the puncture component.

In some embodiments, the attitude adjustment part may further include a plurality of inclination detectors arranged along the peripheral side of the puncture component, and the plurality of inclination detectors may detect an inclination of the puncture component and transmit the inclination of the puncture component to a communication device.

In some embodiments, the attitude adjustment part may further include a locking mechanism including a plurality of electromagnets and a plurality of state detection units corresponding to the plurality of electromagnets, the plurality of electromagnets may be arranged along the peripheral side of the puncture component, the plurality of electromagnets may be connected to the puncture component through power on to lock the puncture component, or the plurality of electromagnets may be disconnected from the puncture component through power off to unlock the puncture component; and the plurality of state detection units may be configured to detect states of the plurality of electromagnets.

In some embodiments, the puncture actuator may include a sliding component, a puncture enabling component disposed on the sliding component, and a linear motion component disposed inside the handle housing, wherein the sliding component may be slidably arranged on the handle housing and connected to the linear motion component, the puncture enabling component may be electrically connected to the communication device, and the puncture enabling component may feedback a puncture enabling signal to an end of a robotic arm through the communication device.

In some embodiments, the sliding component may include a slip ring and a slide block connected to the slip ring, and the slip ring may sleeve an outer side of the handle housing.

In some embodiments, the puncture enabling component may include an enabling trigger key arranged on the slip ring, and when the enabling trigger key is in a triggered state, the puncture enabling signal may be fed back to the end of the robotic arm through the communication device.

In some embodiments, the puncture actuator may include a slide rail, the slide rail may be arranged on an inner wall of the handle housing, the slip ring may slidably sleeve the handle housing, the puncture enabling component may be arranged in the slip ring and the handle housing, and the puncture enabling component may be slidably connected to the slide rail.

In some embodiments, the puncture enabling component may further include a transmitting part and a receiving part arranged at both ends of the puncture component, the transmitting part may emit a photoelectric signal, and the receiving part may receive the photoelectric signal.

In some embodiments, the puncture enabling component may further include a shading block and a press reset key, the slide block may be slidably arranged on the slide rail, the enabling trigger key may be arranged on the slip ring in a pressable manner, the shading block may be connected to the enabling trigger key, and the press reset key may be elastically connected to the shading block and the slide block; and when the enabling trigger key is pressed, the shading block may control the puncture enabling component to transmit the puncture enabling signal to the end of the robotic arm by blocking the photoelectric signal.

In some embodiments, the puncture enabling component may include a puncture trigger switch and a contact wire, one end of the puncture trigger switch may be connected to the enabling trigger key, another end of the puncture trigger switch may be contacted with or separated from the contact wire, and the contact wire may be electrically connected to the communication device; and when the enabling trigger key is pressed, the puncture trigger switch may be separated from the contact wire, and the contact wire may transmit the puncture enabling signal to the end of the robotic arm through the communication device.

In some embodiments, the puncturing trigger switch may be rotatably arranged on the handle housing, the puncture trigger switch may have a rotation center located in a middle of the puncture trigger switch, and the puncture trigger switch may rotate around the rotation center In some embodiments, the puncture enabling component may include the press reset key configured to reset the enabling trigger key, and the press reset key may be arranged on the puncture trigger switch and a support part inside the handle housing.

In some embodiments, the linear motion component may include a first roller, a second roller spaced apart from the first roller, and a connecting rope connecting the first roller and the second roller, the slide block being connected to the connecting rope.

In some embodiments, the force feedback mechanism may include a mounting component and a force feedback component, the force feedback component may be connected to the linear motion component, the mounting component may be installed on a bottom of the handle housing and configured to install the force feedback component, the linear motion component may be arranged on the handle housing and connected to the slide block, and the force feedback component may apply resistance to the linear motion component.

In some embodiments, the first roller may be rotatably arranged on an end of the handle housing away from the mounting component, and the second roller may be rotatably arranged on the mounting component; and the puncture enabling component may further include a mounting base and a fixing part, the mounting base may connect the slide block and the slip ring, and the connecting rope may be fixed to the mounting base through the fixing part.

In some embodiments, the force feedback component may include an actuator motor and a position detection unit, the actuator motor and the position detection unit may be respectively arranged on an axial end of the second roller, the position detection unit may detect a movement of the slip ring and transmit the movement of the slip ring to the communication device, the actuator motor may convert a puncture force fed back from the end of the robotic arm into a torque, and the torque may be applied to the connecting rope.

In some embodiments, the mounting component may include a mounting base and a fixing base arranged on the mounting base, the mounting base and the fixing base may be enclosed to form a mounting cavity for the second roller, the actuator motor may be fixed on the mounting base, and the position detection unit may protrude through the mounting base.

In some embodiments, the force feedback mechanism may further include two couplings, the actuator motor may be connected to the second roller through one coupling, and the position detection unit may be connected to the second roller through another coupling.

In some embodiments, the linear motion component may further include a first limiter and a second limiter, and the first limiter and the second limiter may be respectively arranged at the first roller and the second roller for limiting a movement displacement of the slip ring.

In some embodiments, a movement distance of the slip ring may be related to a movement distance of a puncture needle at the end of the robotic arm.

In some embodiments, the puncture component may include a push rod slidably located in the handle housing and fixedly connected to the slide block.

In some embodiments, the force feedback mechanism may include an air cylinder located at a bottom of a base, the push rod may penetrate through the base to be connected to the air cylinder, and the air cylinder may convert puncture force at the end of the robotic arm into a change of an air pressure value.

In some embodiments, the puncture component may include a displacement sensor located at an end of the puncture component, and the displacement sensor may detect a sliding distance of the slide block sliding along the handle housing and transmit the sliding distance of the slide block to the communication device.

In some embodiments, the puncture component may be a hollow columnar structure, the puncture component may rotate along a spindle of the hollow columnar structure, and the puncture component may be rotatably connected to the attitude adjustment part.

In some embodiments, the master manipulator may include a handle rotation component including a rotation bracket and a rotation bearing mounted between the rotation bracket and the puncture component, the rotation bracket may be mounted on the attitude adjustment part; and the rotation bearing may sleeve an end of the puncture component relatively close to the attitude adjustment part.

In some embodiments, the master manipulator may include a base including a base body and a rotating platform rotatably connected to the base body, the rotating platform may be fixedly connected to the attitude adjustment part, the rotating platform may be parallel to a plane where the base body is located with respect to a rotating plane of the base body, and the rotating platform may be related to at least one joint movement of the robot.

In some embodiments, the base may further include a driving member and a transmission component, and the driving member may drive the rotating platform to rotate through the transmission component.

In some embodiments, the transmission component may include a worm and a worm gear that mesh with each other, the worm may be connected to an output end of the driving member, and the worm may be fixedly connected to the rotating platform.

In some embodiments, the transmission component may include a driving wheel and a driven wheel, a synchronous belt may sleeve the driving wheel and the driven wheel, the driving wheel may be connected to an output end of the driving member, and the driven wheel may be fixedly connected to the rotating platform.

In some embodiments, an encoder may be provided on the rotating platform, and the encoder may detect a rotation angle of the rotating platform and transmit the rotation angle of the rotating platform to the communication device.

In some embodiments, the puncture component may include a connecting rod, a handle, and a depth feedback component, one end of the connecting rod may be movably connected to the base, the handle may be slidably connected to the connecting rod, and the depth feedback component may be electrically connected to the communication device for force feedback and needle insertion control of the handle for depth adjustment.

In some embodiments, the puncture component may further include a screw nut mechanism including a screw rod and a nut, the screw rod may be rotatably mounted inside the connecting rod, a rotation axis of the screw rod may coincide with an axis of the connecting rod, the nut may be movably threadedly connected to the screw rod, the handle may be fixedly connected to the nut, when the handle drives the nut to slide along the axis of the connecting rod, the screw rod may rotate, and the depth feedback component may realize force feedback through the rotation of the screw rod.

In some embodiments, the depth feedback component may include a depth feedback motor, one end of the screw rod may be coaxially and fixedly mounted on an output shaft of the depth feedback motor, and the depth feedback motor may transmit an puncture action of the handle to the end of the robotic arm through a rotation angle change of the depth feedback motor, and adjust a rotation speed of the depth feedback motor according to a contact force on the end of the robotic arm to realize the force feedback.

In some embodiments, the handle may be ring-shaped and may slidably sleeve an outer side of the connecting rod, an inner side of the handle may form a limiting protrusion along an axial direction of the connecting rod, a sidewall of the connecting rod may form a limiting groove along the axial direction of the connecting rod, and the limiting protrusion may be movably arranged in the limiting groove.

The second aspect of the present disclosure further provides a robot, comprising a puncture needle at an end of the robot and any master manipulator of the embodiments of the present disclosure; wherein the puncture needle may be arranged at an end of a robotic arm of the robot, the robot may be electrically connected to a communication device, and the master manipulator may be electrically connected to the communication device and the puncture needle.

Some of the additional features of the present disclosure can be set forth in the following description. Additional features, in part, of the present disclosure will become apparent to those skilled in the art from a study of the following description and accompanying drawings, or from an understanding of the production or operation of the embodiments. The features of the present disclosure can be realized and achieved through the practice or use of the methods, means and combinations of various aspects of the specific embodiments described below.

BRIEF DESCRIPTION OF THE DRAWINGS

The present disclosure will be further illustrated by way of exemplary embodiments. These embodiments will be described in detail with the accompanying drawings. These embodiments are non-limiting. In these embodiments, the same count indicates the same structure, wherein.

DETAILED DESCRIPTION

Figure 1:
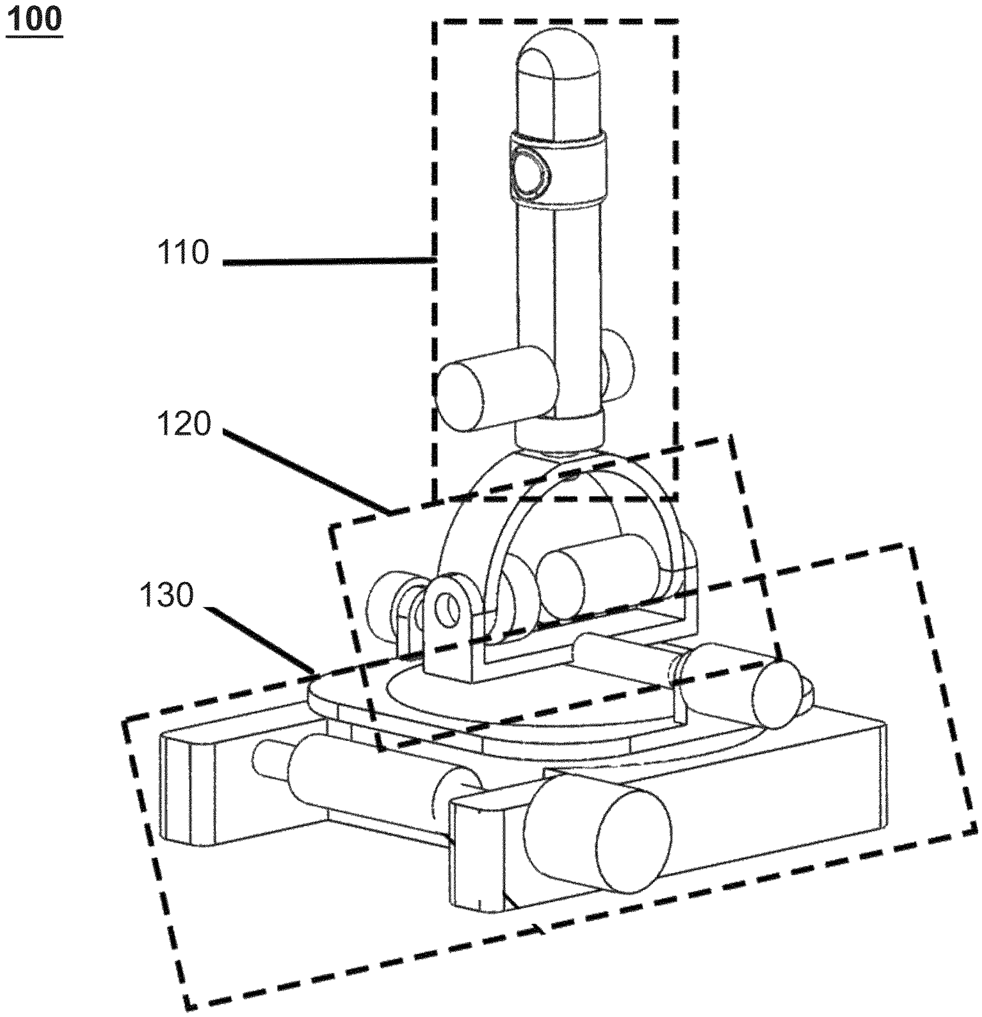
FIG. 1 is a structural diagram illustrating an exemplary master manipulator according to some embodiments of the present disclosure.

In order to more clearly illustrate the technical solutions of the embodiments of the present disclosure, the following briefly introduces the drawings that need to be used in the description of the embodiments. However, it will be apparent to those skilled in the art that the present disclosure may be implemented without these details. In other instances, well-known methods, procedures, systems, components, and/or circuits have been described at a high level in order to avoid unnecessarily obscuring aspects of the disclosure. Apparently, those skilled in the art can make various changes to the disclosed embodiments, and apply the general principles defined in the present disclosure to other embodiments and similar scenarios without deviating from the principles and scope of the present disclosure. Thus, the present disclosure is not intended to be limited to the embodiments shown, but is to be accorded the widest scope consistent with the claims.

The terminology used in the present disclosure is for the purpose of describing certain exemplary embodiments only and is not limiting. As used in the present disclosure, the singular forms "a," "an," and "the" may also include the plural forms unless the context clearly indicates an exception. It should also be understood that the terms "comprising," "comprise," "including," and "include" as used in the specification of the present disclosure only suggest the existence of the stated features, integers, steps, operations, components, and/or parts, but do not exclude the existence or addition of the above other features, integers, steps, operations, components, parts, and/or combinations thereof.

It can be understood that the terms "system," "engine," "unit," "module," and/or "block" used in the present disclosure are used to distinguish different components, elements, parts, portions or assemblies of different levels in an ascending order. However, the words may be replaced by other expressions if other words can achieve the same purpose.

Generally, the words "module," "unit," or "block" as used herein refer to a logic embodied in hardware or firmware, or a collection of software instructions. The modules, units or blocks described in the present disclosure may be implemented as software and/or hardware and stored in any type of non-transitory computer readable medium or other storage devices. In some embodiments, a software module/unit/block may be compiled and linked into an executable program. It will be appreciated that software modules may be called from other modules/units/blocks or themselves, and/or may be called in response to detected events or interrupts. A software module/unit/block configured to be executed on a computing device may be provided on a computer readable medium. For example, a compact disc, a digital video disc, a flash drive, a magnetic disk, or any other tangible medium, or as a digital download (and may be initially stored in a compressed or installable format that requires mounting, decompression, or decryption prior to execution). The software codes herein may be partially or wholly stored in a storage device of a computing device that executes operations, and used in operations of the computing device. The software instructions may be embedded in firmware. It should also be understood that hardware modules/units/blocks may be included in connected logic components, such as gates and flip-flops, and/or may include programmable elements, such as programmable gate arrays or processors. The modules/units/blocks or computing device functions described in the present disclosure may be implemented as software modules/units/blocks, but may be represented in hardware or firmware. In general, the modules/units/blocks described herein refer to logical modules/units/blocks that may be combined with other modules/units/blocks or divided into sub-modules/sub-cells/sub-blocks despite their physical organization or storage devices. The description may apply to a system, an engine, or a portion thereof.

It will be understood that when a unit, an engine, a module, or a block is referred to as being "on," "connected to," or "coupled to" another unit, engine, module, or block, it may be directly on, connected or coupled to, or in communication with another unit, engine, module, or block, or intervening units, engines, modules, or blocks may be present unless the context clearly dictates otherwise. In this application, the term "and/or" may include any one or more of the related listed items or a combination thereof.

These and other features and characteristics of the present disclosure, the function and method of operation of the relevant structural elements, as well as the combination of parts and manufacturing economy will become more apparent from the following description of the accompanying drawings, which constitute a part of the specification of the present disclosure. However, it should be understood that the drawings are for the purposes of illustration and description only, and are not intended to limit the scope of the present disclosure. It should be understood that the drawings are not drawn to scale.

The flowcharts used in the present disclosure illustrate operations that the system implements according to the embodiments of the present disclosure. It should be understood that the foregoing or following operations may not necessarily be performed exactly in order. Instead, the operations may be processed in reverse order or simultaneously. Besides, one or more other operations may be added to these processes, or one or more operations may be removed from these processes.

Some embodiments of the present disclosure provide a master manipulator of a robot. The master manipulator may comprise a puncture component and an attitude adjustment part. The puncture component may include a handle housing, a puncture actuator movably arranged on the handle housing, and a force feedback mechanism arranged at a bottom of the handle housing. The force feedback mechanism and the puncture actuator are connected, and the force feedback mechanism applies resistance to the puncture component based on puncture force feedback information. In some embodiments, the puncture component may be configured to perform a needle insertion control of a puncture needle. The attitude adjustment part may be connected to a bottom of the puncture component to adjust an attitude of the puncture component. In some embodiments, the master manipulator may be applied to the robot, and the master manipulator may remotely control an end of a robotic arm of the robot, so that the puncture needle carried by an end of the robotic arm may penetrate into a target puncture point in a patient's body. Moreover, the robot may be used with an imaging device such as CT, so that a remote puncture operation based on real-time imaging guidance can be realized, and the effects of radiation from the imaging device on the health of a medical staff can be avoided.

The master manipulator provided in the embodiments of the present disclosure can realize a remote control of the end of the robotic arm and the puncture needle provided at the end of the robotic arm. Meanwhile, the master manipulator can also simulate a clinical puncture situation, so that a doctor may feel a needle insertion resistance of the puncture needle, thereby making the whole puncture process safe and efficient, improving the operation accuracy, and thus improving the success rate of puncturing.

FIG. 1 is a structural diagram illustrating an exemplary master manipulator according to some embodiments of the present disclosure.

Referring to FIG. 1, in some embodiments, the master manipulator 100 may include a puncture component 110 and an attitude adjustment part 120. The puncture component 110 may be a main structure that the master manipulator 100 controls a puncture needle at an end of a robotic arm to perform a puncture operation. The puncture component 110 may be a hollow columnar structure for performing a needle insertion control of puncturing. The master manipulator 100 may be in a transmission connection with a robot host of the robot. The transmission connection refers to an electrical connection or a communication connection. The puncture component 110 may feedback a puncture signal to the robot host, so that the robot host may control the end of the robotic arm to prepare for a puncture action. When the puncture component 110 moves, a movement of the puncture component 110 may be fed back to the robot host in real time, and then the robot host may control the end of the robotic arm to drive the puncture needle to perform the puncture operation according to the movement of the puncture component 110.

The attitude adjustment part 120 may be a main structure for the master manipulator 100 to adjust an attitude of the puncture needle. The attitude adjustment part 120 may be connected to a bottom of the puncture component 110, and configured to adjust an attitude of the puncture component 110, and then adjust the attitude of the puncture needle at the end of the robotic arm. When the attitude of the puncture needle is adjusted, the puncture component 110 may rotate relative to the attitude adjustment part 120, and then the attitude adjustment part 120 may detect inclination information of the puncture component 110. After the attitude adjustment part 120 feeds back the inclination information to the robot host, the robot host may adjust the attitude of the end of the robotic arm according to the inclination information of the puncture component 110 to achieve the purpose of adjusting the attitude of the puncture needle, so that the puncture needle may be aligned with a target puncture point, thereby ensuring the accuracy of the puncture operation.

In some embodiments, the master manipulator 100 may further include a base 130. The base 130 may be arranged at a bottom of the attitude adjustment part 120 for supporting and carrying. The base 130 may be provided with a counterweight with a large mass without causing the whole device to shake during operation, and the whole device may remain stable. The base 130 may be in a shape of a flat plate, which is convenient for placing the whole device on a horizontal table for operation. In some embodiments, the base 130 may be rotatable, so as to drive the attitude adjustment part 120 and the puncture component 110 disposed on the base 130 to rotate together, thereby mapping an attitude adjustment plane where the puncture needle at the end of the robotic arm is located. It should be noted that as being used as a platform for supporting and bearing, the base 130 may be applied to the master manipulator 100, and may also be applied to devices of other structures as a base platform.

When the master manipulator 100 performs puncture control, the attitude of the puncture needle in space may be determined according to the target puncture point, then the master manipulator 100 may control the puncture component 110 to rotate a preset angle relative to the attitude adjustment part 120, then the attitude adjustment component 120 may feedback the inclination information to the robot host, and the robot host may adjust the attitude of the puncture needle on the end of the robotic arm according to the inclination information, so that the puncture needle can be aligned with the target puncture point. After the attitude adjustment action is completed, the puncture component 110 may enter a working state, the puncture component 110 may move and feed back to the robot host, and the robot host may control the end of the robotic arm to drive the puncture needle to perform the puncture operation.

In some embodiments, the master manipulator 100 may further include a signal transmission part (not shown in the figure) electrically connected to the puncturing component 110 and the attitude adjustment part 120. The signal transmission part may receive various signals fed back by the puncture component 110 and the attitude adjustment part 120, and output corresponding control signals according to the received signals, to meet the usage requirements of different scenarios (e.g., an attitude adjustment scenario, and a puncture scenario).

In some embodiments, the signal transmission part may be electrically connected to the communication device of the robot, and configured to establish a transmission connection between the master manipulator 100 and the robot host to realize information interaction between the master manipulator 100 and the robot host. That is to say, the information interaction between the master manipulator 100 and the robot host may be realized through the signal transmission part. It can be understood that the information interaction between the various parts of the master manipulator 100 described below (e.g., a puncture enabling component, a force feedback component, etc.) and the robot host may be transmitted between the signal transmission part and the robot host through the communication device. In some embodiments, the signal transmission part may include, but is not limited to, the Ethernet, a serial port, wireless, a CAN bus, an Ether CAT bus, or the like. In the embodiments of the present disclosure, the signal transmission part may realize the information interaction through the Ethernet.

Figure 2:
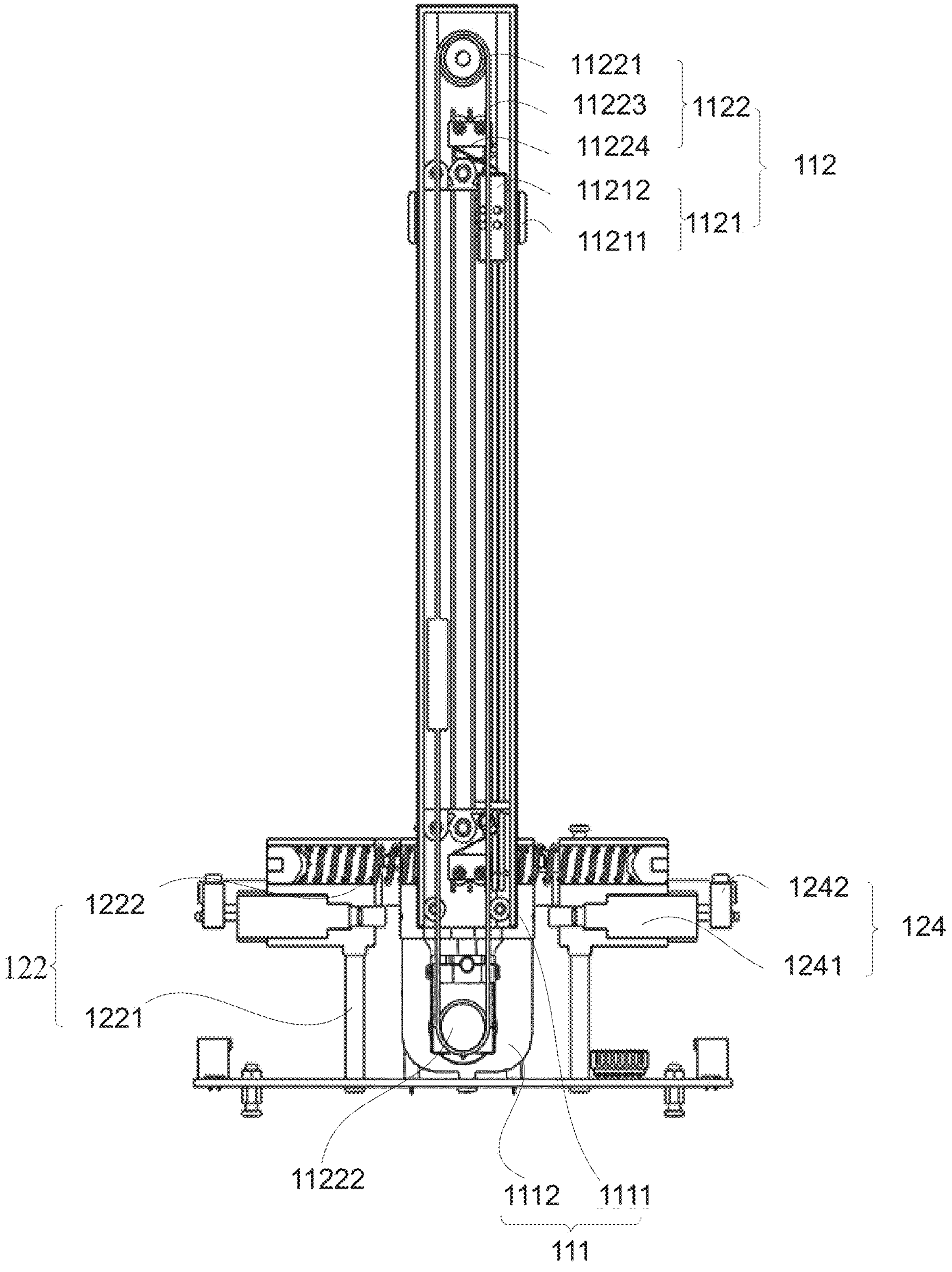
FIG. 2 is a cross-sectional view illustrating a master manipulator according to some embodiments of the present disclosure.
Figure 3:
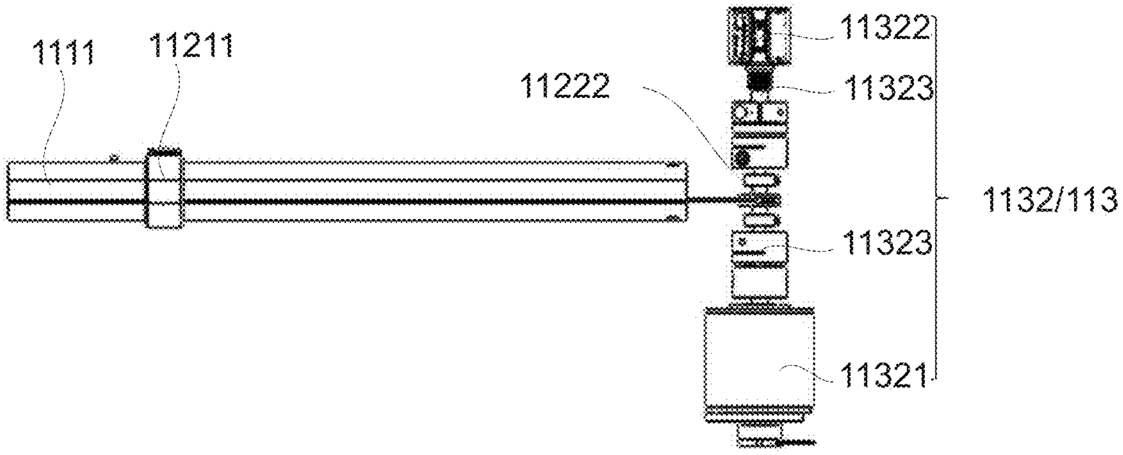
FIG. 3 is a structural diagram illustrating an exemplary puncture component according to some embodiments of the present disclosure.

FIG. 2 is a cross-sectional view illustrating a master manipulator according to some embodiments of the present disclosure. FIG. 3 is a structural diagram illustrating an exemplary puncture component according to some embodiments of the present disclosure.

Referring to FIGS. 2-3, in some embodiments, the puncture component 110 may include a handle housing 111, a puncture actuator 112 movably arranged on the handle housing 111, and a force feedback mechanism arranged at a bottom of the handle housing 111, the force feedback mechanism 113 and the puncture actuator 112 being connected, and the force feedback mechanism 113 applying resistance to the puncture component 110 based on puncture force feedback information. In some embodiments, the force feedback mechanism 113 may be electrically connected to the signal transmission part for performing needle insertion control at the end of the robotic arm, and feeding back the needle insertion resistance at the end of the robotic arm to the puncture actuator 112.

In some embodiments, a bottom of the handle housing 111 may be rotatably installed in the attitude adjustment part 120, and a remaining part of the handle housing 111 may expose out of the attitude adjustment part 120. The doctor may realize puncturing of the puncture needle and attitude adjustment by operating the handle housing 111. The puncture actuator 112 may be partially located in the handle housing 111 and partially expose out of the handle housing 111. The puncture actuator 112 may move relative to the handle housing 111, thereby realizing puncture control of the puncture needle. It can be understood that the puncture actuator 112 may output a linear motion, and after the linear motion is fed back to the robot host, the robot host may control the puncture needle to perform the puncture operation according to a distance of the linear motion output by the puncture actuator 112, so that the puncture needle can smoothly insert into the target puncture point.

In some embodiments, a bottom of the puncture actuator 112 may be connected to the force feedback mechanism 113, and the force feedback mechanism 113 may be in a transmission connection with the robot host through the signal transmission part. The linear motion output by the puncture actuator 112 may be converted into a rotational variable through the force feedback mechanism 113, and fed back to the robot host through the signal transmission part. The robot host may convert the rotational variable into a linear displacement. The robot host may control the movement of the end of the robotic arm according to the linear displacement, so that the end of the robotic arm may drive the puncture needle to perform the puncture operation and accurately insert into the target puncture point. After the puncture operation is completed, the master manipulator 100 may move in a reverse direction of a needle insertion process to realize the withdrawal of the puncture needle from the patient's body. The principle is essentially the same as that of the needle insertion process and will not be repeated here.

It can be understood that there may be a proportional mapping relationship between the linear displacement of the puncture needle and the distance of the linear motion output by the puncture actuator 112, such as 1:1, 1:1.2, 1:1.5, 1:2, 2:1, 1.5:1, 1.2:1, etc. In this way, when the doctor operates the puncture actuator 112 to output the preset distance, they can control the puncture needle to move the preset distance, to truly simulate the clinical puncture situation of the doctor holding the needle for puncturing, improve the operating experience of the doctor, and further improve the success rate of puncturing.

In some embodiments, when the puncture needle is inserted into the patient's body, the human tissue will generate a reaction force against the puncture needle, which is a resistance to puncturing. The resistance may be detected by a sensor at the end of the robotic arm and fed back to the signal transmission part. The signal transmission part may control the force feedback mechanism 113 to apply a force to the puncture actuator 112 according to the resistance fed back from the end of the robotic arm, so that the puncture actuator 112 may feel the resistance to puncturing of the puncture needle when outputting the linear motion, thereby realizing a feedback function of the puncture force. In this way, when the doctor uses the master manipulator 100 to remotely control the puncture needle to perform the puncture operation, the force feedback mechanism 113 may provide the doctor with real-time force feedback, so that the doctor may feel the needle insertion resistance of the puncture needle, thereby making the operation process safer and more efficient.

In some embodiments, the master manipulator 100 may truly simulate the clinical puncture situation through the cooperation of the puncture actuator 112 and the force feedback mechanism 113, which effectively solves the problem that the existing puncture process of the doctor holding the needle cannot be simulated, and the doctor may feel the needle insertion resistance of the puncture needle, thereby making the whole puncture process safer and more efficient, improving the operation accuracy, and thus improving the success rate of puncturing.

Figure 4:
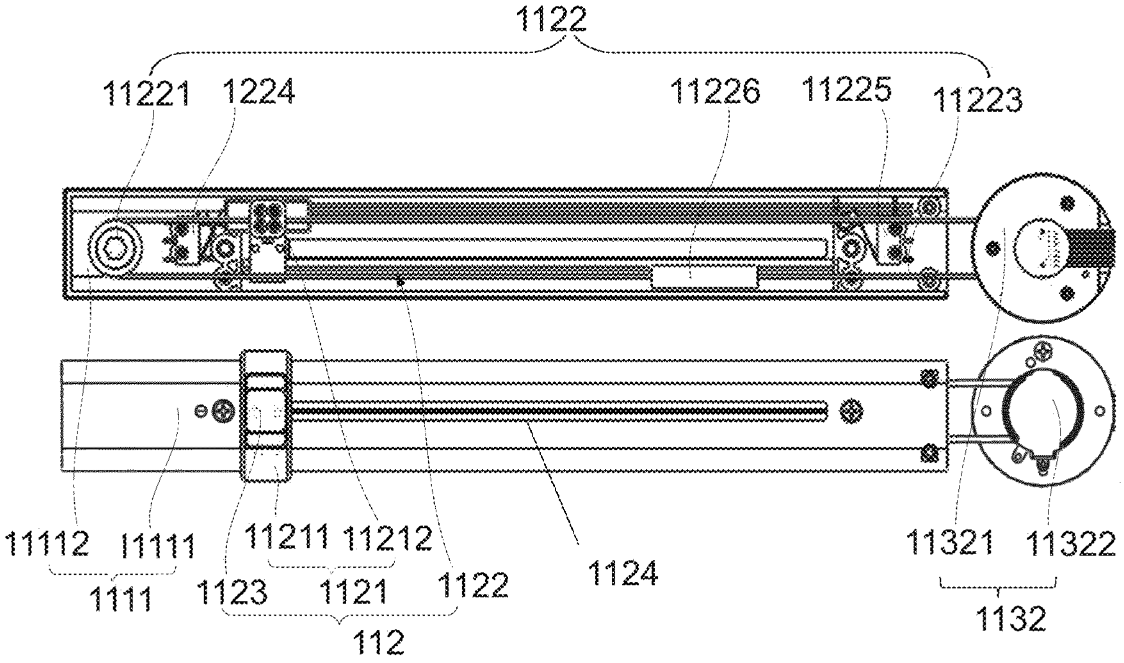
FIG. 4 is a cross-sectional view illustrating a puncture component according to some embodiments of the present disclosure.

FIG. 4 is a cross-sectional view illustrating a puncture component according to some embodiments of the present disclosure.

In some embodiments, referring to FIG. 2 and FIG. 4, the handle housing 111 may include a mounting base 1112 and a handle shell 1111 disposed on the mounting base 1112. The mounting base 1112 may be rotatably disposed on the attitude adjustment part 120 (e.g., an attitude adjustment housing), and the handle shell 1111 may protrude from the attitude adjustment housing. The mounting base 1112 may be arranged at a bottom of the handle shell 1111, and the handle shell 1111 and the attitude adjustment part 120 may be rotatably connected through the mounting base 1112. When the attitude of the puncture needle needs to be adjusted, the handle shell 1111 may rotate relative to the attitude adjustment housing through the mounting base 1112 to realize the adjustment of an angle of the puncture needle.

In some embodiments, the handle shell 1111 may play a protective role, and the puncture actuator 112 (e.g., a linear motion component 1122, and a part of a sliding component 1121 and a puncture enabling component 1123) may be arranged in the handle shell 1111 to avoid exposure, thereby facilitating operation and use. In some embodiments, the handle shell 1111 may include a first housing 11111 and a second housing 11112. The first housing 11111 and the second housing 11112 may be matched and enclosed to form a cavity, and the linear motion component 1122 may be disposed in the cavity.

Referring to FIG. 4, in some embodiments, the puncture actuator 112 may include the sliding component 1121, the puncture enabling component 1123 disposed on the sliding assembly 1121, and the linear motion component 1122 disposed in the handle housing 111. The sliding component 1121 may be slidably disposed on the handle housing 111 and connected to the linear motion component 1122. The puncture enabling component 1123 may be electrically connected to the signal transmission part, so that a puncture signal may be fed back to the end of the robotic arm through the signal transmission part, and the sliding component 1121 may drive the linear motion component 1122 to move.

The sliding component 1121 may be partially disposed in the handle housing 111 and partially disposed outside the handle housing 111. The sliding component 1121 may be connected to the linear motion component 1122 inside the handle housing 111. The puncture enabling component 1123 may be disposed on the sliding component 1121. The linear motion component 1122 may be connected to the force feedback mechanism 113. When the sliding component 1121 performs the linear motion along the handle shell 1111, the sliding component 1121 may drive the linear motion component 1122 to move, so that the linear motion component 1122 may output the linear motion. The force feedback mechanism 113 may convert the linear motion of the sliding component 1121 into the rotational variable, and feedback the rotational variable to the robot host through the signal transmission part to realize the puncture control of the puncture needle.

In some embodiments, when the puncture needle inserts the needle, the resistance may be fed back to the force feedback mechanism 113 through the signal transmission part, and the force feedback mechanism 113 may apply the reaction force to the linear motion component 1122, so that there is the resistance for the sliding component 1121 to drive the movement of the linear motion component 1122, and thus the doctor may feel the needle insertion resistance of the puncture needle when operating the sliding component 1121.

In some embodiments, the puncture enabling component 1123 may realize locking and unlocking on the handle housing 111 through a trigger signal function of the sliding component 1121. The puncture enabling component 1123 may be electrically connected to the signal transmission part. A trigger signal of the puncture enabling component 1123 for locking and unlocking the sliding component 1121 may be fed back to the signal transmission part, and then the signal transmission part may feedback a state of the puncture enabling component 1123 to the robot host, so that the robot host may control the end of the robotic arm to perform a corresponding operation.

In some embodiments, the puncture enabling component 1123 may lock the function of the trigger signal of the sliding component 1121, and the puncturing enabling component 1123 may feedback a signal that it is not ready to puncture to the signal transmission part. In this way, the signal transmission part may not control the end of the robotic arm to move. When the puncture operation is ready, the doctor may operate the puncture enabling component 1123, so that the puncturing enabling component 1123 may unlock the function of the trigger signal of the sliding component 1121. In this case, the puncture enabling component 1123 may feedback a puncture enabling signal ready for puncturing to the signal transmission part, then the signal transmission part may feedback the puncture enabling signal to the robot host, and the robot host may control the end of the robotic arm to prepare for the puncture operation. Then, the sliding component 1121 may drive the puncture enabling component 1123 and the linear motion component 1122 to move to perform the puncture operation. After the puncture operation is completed, the sliding component 1121 may move in an opposite direction, so that the puncture needle may be withdrawn from the patient's body.

In some embodiments, referring to FIG. 4, the sliding component 1121 may include a slip ring 11211 and a slide block 11212 connected to the slip ring 11211. The slip ring 11211 may sleeve an outer side of the handle housing 111. The slip ring 11211 may slide along the handle housing 1111. The slide block 11212 may be connected to the linear motion component 1122, and the slip ring 11211 may drive the linear motion component 1122 to move through the slide block 11212.

Referring to FIG. 3 and FIG. 4, the linear motion component 1122 may include a first roller 11221, a second roller 11222 spaced apart from the first roller 11221, and a connecting rope 11223 connecting the first roller 11221 and the second roller 11222. The slide block 11212 is connected to the connecting rope 11223.

In some embodiments, the first roller 11221 may be arranged at an end of the handle shell 1111, the second roller 11222 may be arranged in the mounting base 1112, and the connecting rope 11223 may surround the first roller 11221 and the second roller 11222. The connecting rope 11223 may drive the first roller 11221 and the second roller 11222 to rotate when the connecting rope 11223 moves. In some embodiments, the connecting rope 11223 may be a steel wire rope. In some embodiments, the linear motion component 1122 may also be a sprocket, a belt drive, or other structures.

The slide block 11212 may be located inside the handle housing 1111 and connected to the connecting rope 11223. Optionally, the slide block 11212 and the connecting rope 11223 may be fixedly connected by components such as a screw plate. When the slip ring 11211 slides along the handle shell 1111, the slip ring 11211 may drive the connecting rope 11223 to move through the slider block 11212, so that the connecting rope 11223 may drive the first roller 11221 and the second roller 11222 to rotate. It can be understood that a cross-sectional shape of the connecting rope 11223 may be a circle, a polygon, an ellipse, or the like, which is not limited. Exemplarily, the cross-sectional shape of the connecting rope 11223 may be a circle or a ribbon shape, or the like.

The force feedback mechanism 113 may be connected to the second roller 11222. When the second roller 11222 rotates, the force feedback mechanism 113 may convert a distance of a linear motion of the slip ring 11211 along the handle shell 1111 into a rotation variable, and feedback the rotation variable to the robot host through the signal transmission part to control the puncture needle for puncturing. Meanwhile, the resistance during the puncture process of the puncture needle may also be fed back to the signal transmission part, and the signal transmission part may control the force feedback mechanism 113 to move according to the resistance, so that an output torque of the force feedback mechanism 113 may act on the second roller 11222. When the slip ring 11211 drives the connecting rope 11223 to move through the slide block 11212, the torque received by the second roller 11222 may apply a reaction force to the movement of the connecting rope 11223. In this way, when the doctor operates the slip ring 11211 to slide, they can feel the resistance generated by the torque applied by the force feedback mechanism 113, which is the needle insertion resistance of the puncture needle, thereby truly simulating the situation of holding the needle for puncturing.

In some embodiments, the linear motion component 1122 may further include a first limiter 11224 and a second limiter 11225. The first limiter 11224 and the second limiter 11225 may be respectively arranged on the first roller 11221 and the second roller 11222 for limiting a movement displacement of the slip ring 11211. The first limiter 11224 and the second limiter 11225 may be located between the first roller 11221 and the second roller 11222, the first limiter 11224 may be set close to the first roller 11221, and the second limiter 11225 may be set close to the second roller 11222. Optionally, the first limiter 11224 and the second limiter 11225 may be limit switches. The positions of the first limiter 11224 and the second limiter 11225 may be limit points of mechanical movement limitation, ensuring that electrical limitation works before mechanical limitation.

The first limiter 11224 and the second limiter 11225 may prevent the slip ring 11211 from overtraveling, ensuring that a movement track of the puncture needle is accurate, and that the puncturing of the puncture needle does not exceed the displacement, thereby avoiding accidents. When the slip ring 11211 drives the slide block 11212 to move to the second limiter 11225, and the second limiter 11225 detects the slip ring 11211, it indicates that the slide block 11212 moves to a limit position, and the puncture needle stops advancing. In this case, a tip of the puncture needle is positioned at the target puncture point. When the slip ring 11211 drives the slide block 11212 to the first limiter 11224, and the first limiter 11224 detects the slide block 11212, it indicates that the slip ring 11211 moves to a limit position. In this case, the puncture needle completes withdrawing the needle.

In some embodiments, the first limiter 11224 and the second limiter 11225 may be electrically connected to the signal transmission part. The first limiter 11224 and the second limiter 11225 may automatically identify the limit position of the slide block 11212 and feedback the limit position of the slide block 11212 to the signal transmission part. When the slide block 11212 moves to any of the limit positions, the signal transmission part may control the actuator motor 11321 to move to limit continuous movement of the slip ring 11211.

In some embodiments, a movement distance of the slip ring 11211 may be related to a movement distance of the end of the robotic arm. For example, when the master manipulator 100 simulates the puncture movement, a 1:1 mapping relationship with the end of the robotic arm may be realized, i.e., when the slip ring 11211 moves, the puncture needle at the end of the robotic arm may move equidistantly, thereby better simulating the puncture action at the end of the master manipulator, and improving the success rate of puncturing. In some embodiments, when the master manipulator 100 simulates the puncture movement, other mapping relationships with the end of the robotic arm may also be realized, for example, 1:1.2, 1:1.5, 1:2, 2:1, 1.5:1, 1.2:1, etc. A mapping ratio of the movement distance of the slip ring 11211 to the movement distance of the end of the robotic arm may be adjusted in software control.

In some embodiments, the linear motion component 1122 may also include a tension spring 11226 which is arranged on the connecting rope 11223 and is configured to keep the connecting rope 11223 in a tensioned state, so that the slide block 11212 may drive the connecting rope 11223 to drive the first roller 11221 and the second roller 11222 to rotate, ensuring that the distance of the linear motion of the slip ring 11211 may be accurately converted into the linear displacement of the puncture needle, and that the puncture needle may accurately insert into the target puncture point.

Figure 5:
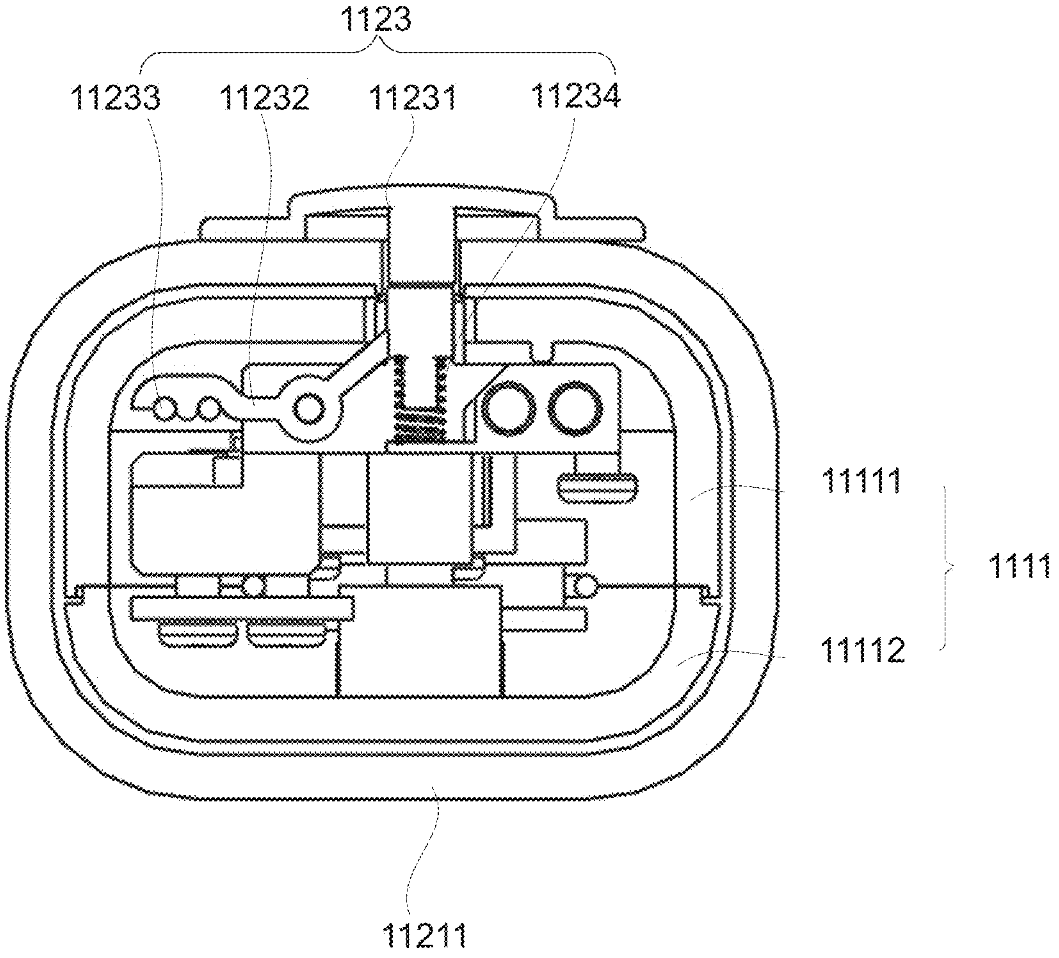
FIG. 5 is a structural diagram illustrating an exemplary puncture enabling component according to some embodiments of the present disclosure.

FIG. 5 is a structural diagram illustrating an exemplary puncture enabling component according to some embodiments of the present disclosure.

Referring to FIG. 4 and FIG. 5, in some embodiments, the puncture enabling component 1123 may include an enabling trigger key 11231. The enabling trigger key 11231 may be arranged on the slip ring 11211. When the enabling trigger key 11231 is in a triggered state, a puncture enabling signal may be fed back to the robot through the signal transmission part.

In some embodiments, the slip ring 11211 may have a through hole communicating with the handle housing 111.

The enabling trigger key 11231 may be disposed in the through hole, and protrude from the slip ring 11211. Optionally, the enabling trigger key 11231 may be arranged on the slip ring 11211 by gluing or other means. The slip ring 11211 may move up and down on the handle housing 111 by holding the slip ring 11211 and controlling whether to trigger the enabling trigger key 11231, thereby simulating the puncture process. The slip ring 11211 may only slide along the handle housing 111 when the enabling trigger key 11231 is triggered. Otherwise, the slip ring 11211 is fixed.

In some embodiments, a trigger mode of enabling trigger key 11231 may be a push trigger. For example, the enabling trigger key 11231 may be disposed in the through hole of the slip ring 11211 in a pressable manner. The enabling trigger key 11231 may be pressed to be in the triggered state. In some embodiments, the trigger mode of the enabling trigger key 11231 may also be an inductive trigger. For example, an inductive switch may be provided at a position of the enabling trigger key 11231 protruding from the slip ring 11211, and triggering of the enabling trigger key 11231 may be realized by controlling the inductive switch.

In some embodiments, referring to FIG. 4, the puncture actuator 112 may further include a slide rail 1124. The slide rail 1124 may be disposed on an inner wall of the handle housing 111. The slip ring 11211 may slidably sleeve on the handle housing 111. The puncture enabling component 1123 may be disposed in the slip ring 11211 and the handle housing 111, and slidably connected to the slide rail 1124. When the puncture enabling component 1123 is triggered, the slip ring 11211 may slide along the slide rail 1124 through the puncturing enabling component 1123. The slide block 11212 may be slidably disposed on the slide rail 1124. The slide block 11212 may be fixedly connected to the slip ring 11211. When the slip ring 11211 slides along the handle housing 111, the slip ring 11211 may drive the slider block 11212 to slide along the slide rail 1124, ensuring that movement track of the slip ring 11211 is accurate, avoiding translocation of the slip ring 11211, and reducing a frictional force of the slip ring 11211 during sliding. Optionally, the slip ring 11211 may be fixed on the slide block 11212 through a threaded part or the like.

The slip ring 11211 may sleeve an outer side of the handle housing 111, and the slip ring 11211 may slide along an outer shell of the handle housing 111. When the slip ring 11211 slides, the force feedback mechanism 113 may detect the movement of the slip ring 11211, and then feedback the movement of the slip ring 11211 to the robot host through a master control board, and the robot host may control the end of the robotic arm to drive the puncture needle to move. When the enabling trigger key 11231 is triggered, the slip ring 11211 may move along the handle housing 111, and after triggering the enabling trigger key 11231 is stopped, the slip ring 11211 may be fixed at the position of the handle housing 111. Moreover, the movement displacement of the slip ring 11211 may be determined by a displacement of the puncture needle at the end of the robotic arm. Of course, a certain enlargement or reduction ratio may also be set to reduce or increase the overall displacement of the master manipulator.

The slide rail 1124 may be disposed on the inner wall of the handle housing 111. The slide rail 1124 may guide the movement of the slip ring 11211 to prevent the position of the slip ring 11211 from dislocating when the slip ring 11211 slides along the handle housing 111 and ensure that the slip ring 11211 can accurately control the movement of the puncture needle. The puncture enabling component 1123 may be disposed in the handle shell 111, and the puncture enabling component 1123 may connect the slip ring 11211 and the slide rail 1124. The slip ring 11211 may be slidably connected to the slide rail 1124 through the puncture enabling component 1123 to guide the movement of the slide rail 1124.

In some embodiments, referring to FIG. 5, the puncture enabling component 1123 may further include a puncture trigger switch 11232 and a contact wire 11233. The puncture trigger switch 11232 may be rotatably arranged on the handle housing 111. One end of the puncture trigger switch 11232 may be connected to the enabling trigger key 11231, and another end of the puncture trigger switch 11232 may be contacted with or separated from the contact wire 11233. When the puncture trigger switch 11232 is separated from the contact wire 11233, a puncture signal may be sent to the end of the robotic arm.

The enabling trigger key 11231 refers to a key for the puncture component 110 to send a puncture preparation. A mounting hole may be provided on the slip ring 11211. A chute along a sliding direction may be provided on the handle housing 1111. The enabling trigger key 11231 may be installed in the mounting hole of the slip ring 11211. A portion (e.g., a press portion) of the enabling trigger key 11231 may be exposed out of the slip ring 11211 to facilitate the doctor to perform a trigger operation. The puncture trigger switch 11232 may be rotatably arranged in the handle shell 1111. The puncture trigger switch 11232 may have a rotation center which is located in a middle of the puncture trigger switch. The puncture trigger switch may rotate around the rotation center.

Taking triggering by pressing mode as an example, when the doctor presses the enabling trigger key 11231, the enabling trigger key 11231 may press one end of the puncture trigger switch 11232, so that the puncture trigger switch 11232 may rotate, and when the puncture trigger switch 11232 rotates, the other end of the puncture trigger switch 11232 may be separated from the contact wire 11233. When the doctor releases the enabling trigger key 11231, the press portion of the enabling trigger key 11231 may be exposed out of the slip ring 11211, and then one end of the puncture trigger switch 11232 may also move with the enabling trigger key 11231, so that the other end of the puncture trigger switch 11232 may be contacted with the contact wire 11233.

The contact wire 11233 may be electrically connected to the signal transmission part. When the puncture trigger switch 11232 is contacted with the contact wire 11233, the contact wire 11233 may not send a puncture enabling signal to the signal transmission part, and then the signal transmission part may not send the puncture enabling signal to the robot host, which indicates that the puncture operation is not ready. When the enabling trigger key 11231 is pressed, the enabling trigger key 11231 may drive the trigger switch to be separated from the contact wire 11233, the contact wire 11233 may send the puncture enabling signal to the robot host through the signal transmission part, and the robot host may drive the end of the robotic arm to move, so that the end of the robotic arm may drive the puncture needle to prepare for the needle insertion action.

It can be understood that when the puncture enabling component 1123 is at an initial position, the puncture trigger switch 11232 may always be contacted with the contact wire 11233. Only by pressing the enabling trigger key 11231, the puncture trigger switch 11232 may be separated from the contact wire 11233. That is to say, the puncture enabling component 1123 is based on the principle of a normally-closed switch. In this way, the puncture component 110 may send the puncture enabling signal, and then the end of the robotic arm may work, thereby ensuring the safety of the operation.

In some embodiments, the puncture trigger switch 11232 may be installed in the handle shell 1111 through a fixing shaft. The puncture trigger switch 11232 may rotate around the fixing shaft. Optionally, the puncture trigger switch 11232 may be a metal rotating member (i.e., a conductor). The contact wire 11233 may be two metal rods. Under normal conditions, the puncture trigger switch 11232 may be connected to the contact wire 11233, and the circuit is connected. When the enabling trigger key 11231 is triggered, the puncture trigger switch 11232 may be separated from the contact wire 11233, and the circuit is disconnected.

Referring to FIG. 5, in some embodiments, the puncture enabling component 1123 may further include an enabling reset member 11234 which is arranged on a support part inside the puncture trigger switch 11232 and the handle shell 1111. The enabling reset member 11234 may be configured to automatically reset the enabling trigger key 11231. When the enabling trigger key 11231 is pressed, the enabling trigger key 11231 may overcome an elastic force of the enabling reset member 11234 to drive the puncture trigger switch 11232 to move, so that the puncture trigger switch 11232 may be separated from the contact wire 11233, and then the slip ring 11211 may move along the handle shell 1111. When the slip ring 11211 moves in place, the enabling trigger key 11231 may be released, and the enabling reset member 11234 may drive the puncture trigger switch 11232 and the enabling trigger key 11231 to reset automatically. Optionally, the enabling reset member 11234 may be a spring.

In some embodiments, the puncturing component 110 may also send the puncture enabling signal to the robot host using photoelectric communication, so that the robot host may drive the end of the robotic arm to move, thereby driving the puncture needle to prepare for needle insertion.

Figure 6:
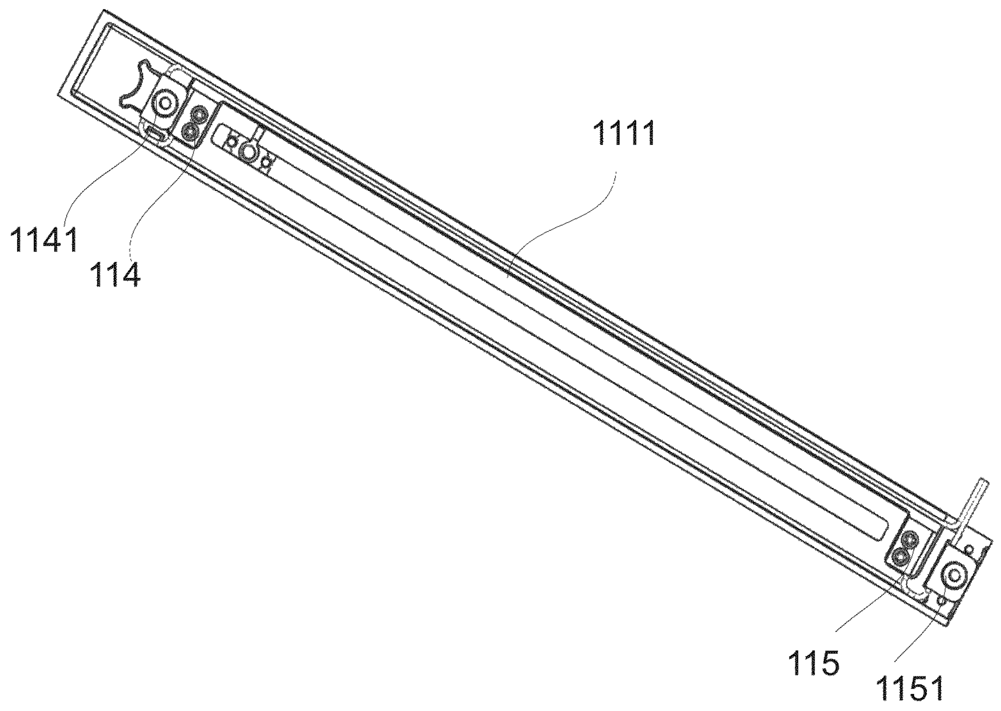
FIG. 6 is a structural diagram illustrating an exemplary puncture component according to some embodiments of the present disclosure.

FIG. 6 is a structural diagram illustrating an exemplary puncture component according to some embodiments of the present disclosure.

Referring to FIG. 6, in some embodiments, the puncture component 110 may further include a transmitting part 114 and a receiving part 115 disposed at both ends of the handle housing 111. The transmitting part 114 may be configured to transmit a transmission light path, and the transmission light path may be received by the receiving part 115. The puncture enabling component 1123 may move to the transmission light path between the transmitting part 114 and the receiving part 115, or away from the transmission light path between the transmitting part 114 and the receiving part 115. After the puncture enabling component 1123 is pressed, the puncture enabling component 1123 may block the transmission light path.

Figure 7:
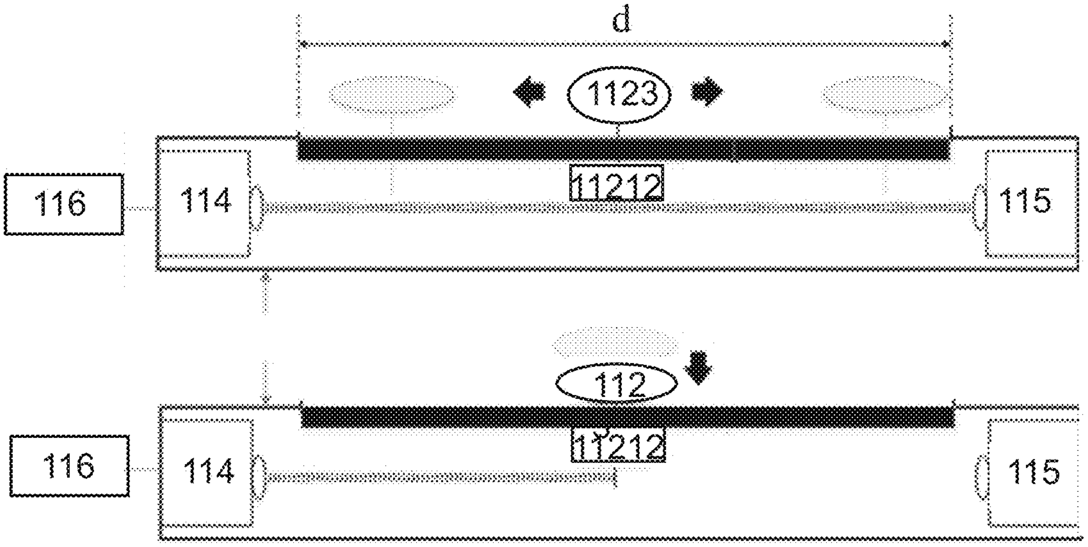
FIG. 7 is a schematic diagram illustrating a working principle of a puncture enabling component cooperating with a transmitting part and a receiving part according to some embodiments of the present disclosure.

FIG. 7 is a schematic diagram illustrating a working principle of a puncture enabling component cooperating with a transmitting part and a receiving part according to some embodiments of the present disclosure.

Referring to FIG. 6 and FIG. 7, the transmitting part 114 and the receiving part 115 may be disposed at both ends of the handle housing 111. A distance between the transmitting part 114 and the receiving part 115 may be greater than a movement displacement of the slip ring 11211. The transmitting part 114 may transmit the transmission light path, and the transmission light path may be received through the receiving part 115. In some embodiments, the puncture component 110 may further include a conduction member for conducting the transmitting part 114 and the receiving part 115. The transmitting part 114 and the receiving part 115 may be conducted through the conduction member, and the transmitting part 114 and the receiving part 115 may be respectively connected to an end amplifier 116 to facilitate signal transmission. Optionally, the conduction member may be an optical fiber.

It is worth noting that the puncture component 110 of the master manipulator 100 may realize non-contact needle insertion control through the transmitting part 114 and the receiving part 115. When the puncture enabling component 1123 is pressed, a shading block 11235 of the puncture enabling component 1123 may block the transmission light path emitted by the transmitting part 114, so that a level state in the receiving part 115 may change, thereby triggering the puncture signal. When the puncture enabling component 1123 is released, the transmission light path may be reconducted, thereby ending a puncture state.

When the puncture enabling component 1123 is pressed, the puncture enabling component 1123 may move to a position between the transmitting part 114 and the receiving part 115, the puncture enabling component 1123 may block the transmission light path emitted by the transmitting part 114, and the receiving part 115 may not receive the transmission light path, which indicates that the puncture operation can be performed. In this case, the receiving end may send the puncture signal to the robot host through the signal transmission part, which indicates that the puncture movement may start. When the puncture enabling component 1123 is released, the puncture enabling component 1123 may be far away from the transmission light path emitted by the transmitting part 114, and the puncture enabling component 1123 may no longer block the transmission light path. After the receiving end receives the transmission light path, a stop signal may be sent to the robot body through the signal transmission part, which indicates that the puncture movement may stop.

In some embodiments, the transmitting part 114 and the receiving part 115 may constitute a light sensor, wherein the transmitting part 114 may be a transmitting end, and the receiving part 115 may be a receiving end. The transmitting part 114 and the receiving part 115 may be connected through an optical fiber.

Specifically, the slide rail 1124 may be disposed on the inner wall of the handle shell 1111 along a length direction of the handle housing 111. The transmitting part 114 may be fixed on one end of the handle shell 1111 through a first wire pressing plate 1141, and the receiving part 115 may be fixed on another end of the handle shell 1111 through a second wire pressing plate 1151. Moreover, the inner wall of the handle shell 1111 may be provided with a wire slot for fixing the conduction member. A connecting plate may be prevented from being separated from the wire slot by the first wire pressing plate 1141 and the second wire pressing plate 1151, thereby ensuring the working reliability of the signal transmission part.

Figure 8:
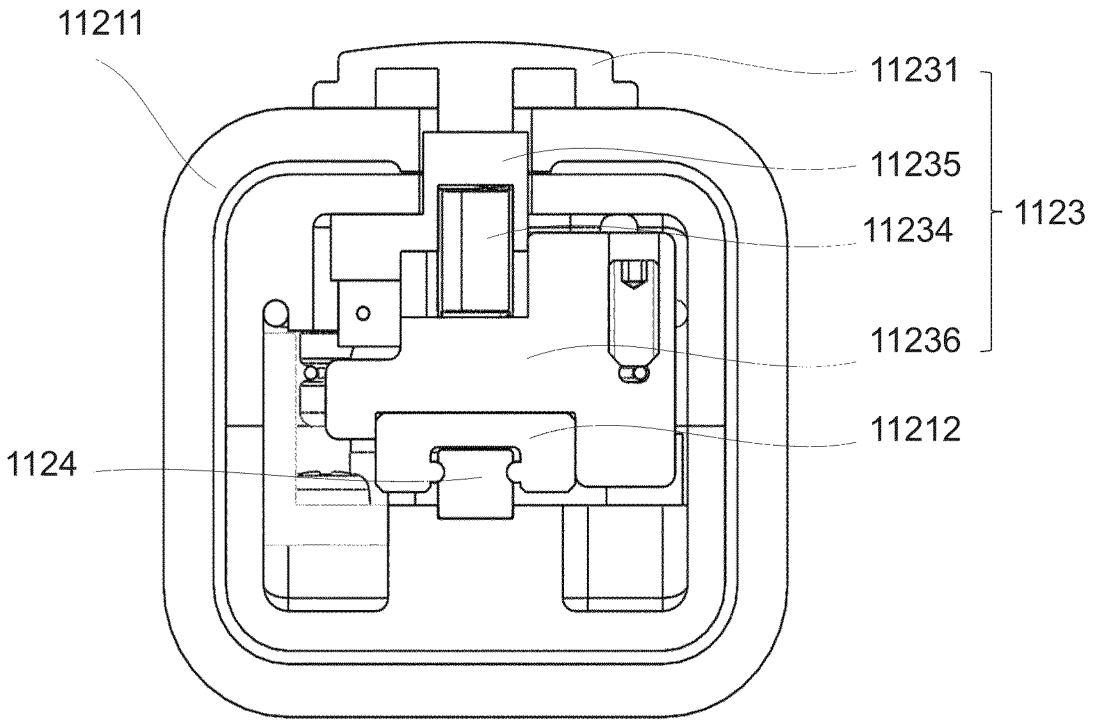
FIG. 8 is a structural diagram illustrating an exemplary puncture enabling component according to some embodiments of the present disclosure.

FIG. 8 is a structural diagram illustrating an exemplary puncture enabling component according to some embodiments of the present disclosure.

Referring to FIG. 8, in some embodiments, the puncture enabling component 1123 may further include a shading block 11235. The slide block 11212 may be slidably disposed on the slide rail 1124. The enabling trigger key 11231 may be disposed on the slip ring 11211 in a pressable manner. The shading block 11235 may be movably arranged in the handle housing 111 and connected to the enabling trigger key 11231. The enabling reset member 11234 may elastically connect the shading block 11235 and the slide block 11212. When the enabling trigger key 11231 is pressed, the shading block 11235 may block a transmission signal.

The enabling trigger key 11231 may be connected to the shading block 11235 in the through hole of the slip ring 11211. The enabling trigger key 11231 may drive the shading block 11235 to reciprocate in the handle housing 111, so that the shading block 11235 may be located in the transmission light path or away from the transmission light path. In the initial state (i.e., when the enabling trigger key 11231 is not pressed), there may be a certain space between the shading block 11235 and the slide block 11212, and this space may allow the transmission light path to pass through. When the enabling trigger key 11231 is pressed, the shading block 11235 may block the space, thereby blocking the transmission light path.

It should be noted that a structural form of the shading block 11235 may not be limited, as long as the light path may be blocked. When the enabling trigger key 11231 is pressed, the enabling trigger key 11231 may retract the slip ring 11211 and drive the shading block 11235 to move to the transmission light path to block the transmission light path, so that the signal transmission part may send a puncture enabling signal. When the enabling trigger key 11231 is released, the enabling trigger key 11231 and the shading block 11235 may reset, the enabling trigger key 11231 may protrude from the slip ring 11211, the shading block 11235 may move in the handle housing 111 to separate from the transmission light path, and the transmission light path may be conducted. In this case, the signal transmission part may no longer send the puncture enabling signal.

The enabling reset member 11234 may be provided between the shading block 11235 and the slide block 11212, and the enabling trigger key 11231 and the shading block 11235 may automatically reset through the enabling reset member 11234, thereby ensuring the accuracy of the operation process. Specifically, one end of the enabling reset member 11234 may be connected to the shading block 11235, and another end of the enabling reset member 11234 may be connected to the slide block 11212. When the enabling trigger key 11231 is pressed, the enabling trigger key 11231 may overcome the elastic force of the enabling reset member 11234 and drive the shading block 11235 to move to block the transmission light path. When the enabling trigger key 11231 is released, the elastic force of the enabling reset member 11234 may drive the shading block 11235 and enabling trigger key 11231 to reset, so that the shading block 11235 may no longer block the transmission light path.

In some embodiments, the puncture enabling component 1123 may further include a mounting part 11236 and a fixing part. The mounting part 11236 may connect the slide block 11212 and the slip ring 11211. The fixing part may be configured to fix the connecting rope 11223 to the mounting part 11236. The mounting part 11236 may be fixed on the slide block 11212 and configured to increase a contact area of the slide block 11212 to facilitate a connection of the slide block 11212 with the slip ring 11211 and other parts of the puncture enabling component 1123. In some embodiments, the mounting part 11236 and the slide block 11212 may be integrated, or the mounting part 11236 and the slide block 11212 may also be detachably connected.

The mounting part 11236 may be fixed on the slide block 11212. The mounting part 11236 may be connected to the slip ring 11211. There may be a space between the mounting part 11236 and the shading block 11235, and the enabling reset member 11234 may be installed in the space. Moreover, the mounting part 11236 may also has a through hole for the connecting rope 11223 to pass through, and the fixing part may fix the connecting rope 11223 on the mounting part 11236. In this way, when the slip ring 11211 drives the slide block 11212 to move, the slip ring 11211 may drive the connecting rope 11223 to move synchronously through the mounting part 11236. Optionally, the fixing part may include a threaded part, a pressing plate, or the like.

Figure 9:
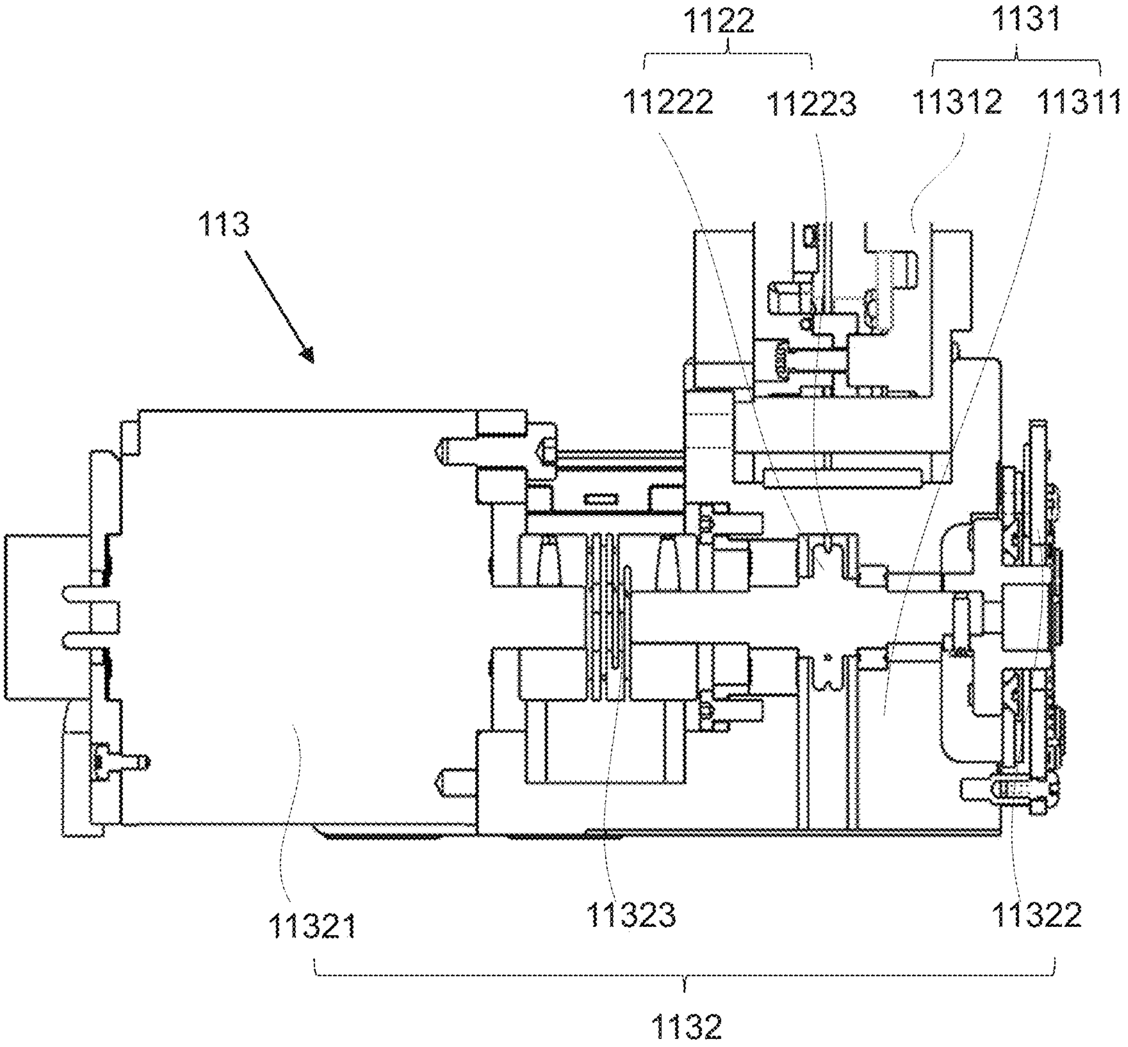
FIG. 9 is a structural diagram illustrating an exemplary force feedback mechanism according to some embodiments of the present disclosure.

FIG. 9 is a structural diagram illustrating an exemplary force feedback mechanism according to some embodiments of the present disclosure.

Referring to FIG. 9, the force feedback mechanism 113 may include a mounting component 1131 and a force feedback component 1132. The force feedback component 1132 may be connected to the linear motion component 1122. The mounting component 1131 may be installed on a bottom of the handle housing 111 for mounting the force feedback component 1132. The linear motion component 1122 may be disposed on the handle housing 111 and connected to the slide block 11212. The force feedback component 1132 may apply a resistance to the linear motion component 1122.

In some embodiments, the mounting component 1131 may function as a support. The mounting component 1131 may be disposed on the bottom of the handle housing 111 for mounting each component of the puncture component 110. Specifically, a portion of the linear motion component 1122 may be disposed in the handle shell 1111 of the handle housing 111, and the bottom of the linear motion component 1122 may be movably disposed in the mounting component 1131. The force feedback component 1132 may be movably mounted on the mounting component 1131. The force feedback component 1132 may be connected to the linear motion component 1122. The force feedback component 1132 may detect the movement displacement of the slip ring 11211 and apply the resistance to the slip ring 11211 through the slide block 11212 by the linear motion component 1122, to simulate the needle insertion resistance of the puncture needle.

When the slip ring 11211 performs a linear motion, the force feedback component 1132 may detect a distance of the linear motion of the slip ring 11211, and feedback the distance of the linear motion of the slip ring 11211 to the robot host through the signal transmission part. The robot host may convert the distance of the linear motion of the slip ring 11211 into a linear displacement. The end of the robotic arm may be controlled through the linear displacement to drive the puncture needle to perform the puncture operation.

In some embodiments, when the puncture needle inserts into the patient's body, the human body tissue will generate a reaction force on the puncture needle, which is the puncture resistance. The resistance may be detected by a sensor at the end of the robotic arm and fed back to the force feedback component 1132 through the signal transmission part. The force feedback component 1132 may apply the reaction force to the linear motion component 1122, so that the movement of the linear motion component 1122 driven by the slip ring 11211 has the resistance. In this way, when the doctor operates the slip ring 11211, the doctor may feel the needle insertion resistance of the puncture needle.

In some embodiments, the first roller 11221 of the linear motion component 1122 may be rotatably disposed on an end of the handle housing 111 away from the mounting component 1131, and the second rolling wheel 11222 of the linear motion component 1122 may be rotatably disposed on the mounting component 1131. The force feedback component 1132 may be connected to the second roller 11222.

When the second roller 11222 rotates, the force feedback component 1132 may detect the distance of the linear motion of the slip ring 11211 along the handle housing 111, and feedback the distance of the linear motion of the slip ring 11211 to the robot host through the signal transmission part to control the puncture needle for puncturing. Meanwhile, the resistance during the puncture process of the puncture needle may also be fed back to the signal transmission part, and the signal transmission part may control the movement of the force feedback component 1132 according to the resistance, so that the output torque of the force feedback component 1132 may act on the second roller 11222. When the slip ring 11211 drives the connecting rope 11223 to move through the slide block 11212, the torque received by the second roller 11222 may apply a reaction force to the movement of the connecting rope 11223. In this way, when the doctor operates the slip ring 11211 to slide, the doctor may feel the resistance generated by the torque applied by the force feedback component 1132, which is the needle insertion resistance of the puncture needle, thereby truly simulating the situation of holding the needle for puncturing.

Referring to FIG. 9, in some embodiments, the force feedback component 1132 may include an actuator motor 11321 and a position detection unit 11322. The second roller 11222 may be respectively connected to the actuator motor 11321 and the position detection unit 11322. The position detection unit 11322 may detect a movement of the slip ring 11211 and transmit the movement of the slip ring 11211 to the communication device. The actuator motor 11321 may convert the puncture force fed back from the end of the robotic arm into a torque and apply the torque to the connecting rope 11223.

In some embodiments, referring to FIG. 3 and FIG. 9, the force feedback component 1132 may further include two couplings 11323. One coupling 11323 may be connected to the actuator motor 11321 and the second roller 11222, and another coupling 11323 may be connected to the position detection unit 11322 and the second roller 11222. After the coupling 11323 is connected to the second roller 11222 and the actuator motor 11321, there may be no transmission link between the second roller 11222 and the actuator motor 11321, thereby ensuring the transmission efficiency, reducing the frictional resistance, and improving the fidelity of the puncture force feedback. A current position state of the slide block 11212 may be detected and the movement displacement of the slide block 11212 may be identified by the position detection unit 11322, and fed back to the robot host through the signal transmission part. Exemplarily, the position detection unit 11322 may be a potentiometer, and the movement displacement of the slide block 11212 may be identified through the potentiometer. In other embodiments of the present disclosure, the position detection unit 11322 may also be a sensor or other components, and its working principle is substantially the same as that of the potentiometer, which is not repeated here.

When the position detection unit 11322 is the potentiometer, the potentiometer may detect the displacement of the linear motion of the slip ring 11211 and convert the movement of the slip ring 11211 into a rotational variable. The potentiometer may be electrically connected to the signal transmission part, and the rotational variable of the potentiometer may be fed back to the robot host through the signal transmission part. The robot host may convert the rotational variable into the linear displacement of the puncture needle, and then control the end of the robotic arm to drive the puncture needle to perform the linear displacement, so that the puncture needle may insert into the target puncture point.

The actuator motor 11321 may be electrically connected to the signal transmission part. During the puncture process of the puncture needle, the resistance when the puncture needle is in contact with human tissue may be detected by the sensor at the end of the robotic arm. The sensor may feedback the need insertion resistance to the robot host, and then the robot host may feedback the resistance to the signal transmission part. The signal transmission part may control the actuator motor 11321 to apply a certain current to generate a torque to act on the second roller 11222, and then the second roller 11222 may apply the resistance to the connecting rope 11223. The resistance generated by the torque may be consistent with the actual needle insertion resistance of the puncture needle. The resistance on the connecting rope 11223 may act on the hand of the doctor through the slip ring 11211, and the doctor may feel the resistance when moving the slip ring 11211, thereby realizing the feedback function of the puncture force.

It is worth noting that when the enabling trigger key 11231 is triggered, it indicates that the device is ready for puncturing. When the doctor pushes down the slip ring 11211, the slip ring 11211 may be subjected to the resistance due to the effect of the actuator motor 11321. This resistance is formed by the superposition of an output resistance of the actuator motor 11321 and a resistance of the equipment system. Generally, the resistance of the equipment system is small and may be ignored, and the force experienced by the doctor depends on the resistance of the actuator motor 11321. During the puncture process of the robot, on-site resistance data may be fed back to the signal transmission part through the robot host. The signal transmission part may adjust the current of the actuator motor 11321, and then finally transmit the resistance to the slip ring 11211. Finally, the hand holding the slip ring 11211 may experience the force feedback to a puncture injury.

In some embodiments, the puncture component 110 may also include a reset key arranged on the attitude adjustment housing 121 of the attitude adjustment part 120. The reset key may be electrically connected to the signal transmission part, and electrically connected to the actuator motor through the signal transmission part 11321. After the puncture operation is completed, the reset key may be operated to control the movement of the actuator motor 11321 through the signal transmission part, so that the actuator motor 11321 may drive the slide block 11212 and reset the slip ring 11211 through the second roller 11222 and the connecting rope 11223, thereby withdrawing the puncture needle from the patient's body. Of course, in other embodiments of the present disclosure, a needle withdrawal operation of the puncture needle may also be realized through the reverse movement of the slip ring 11211 along the handle shell 1111. The puncture component 110 may control the puncture needle to realize the needle insertion operation in the above-mentioned manner until the end of the puncture needle moves to the target puncture point, and then the puncture component 110 stops working. In this case, the puncture needle may perform inspection or treatment, or the like on the target puncture point. After the puncture operation is completed, the puncture needle may be withdrawn from the patient's body according to the reverse movement of the slip ring 11211, and the automatic reset of the slip ring 11211 may also be realized through the reset key to realize automatic withdrawal of the puncture needle.

Figure 13:
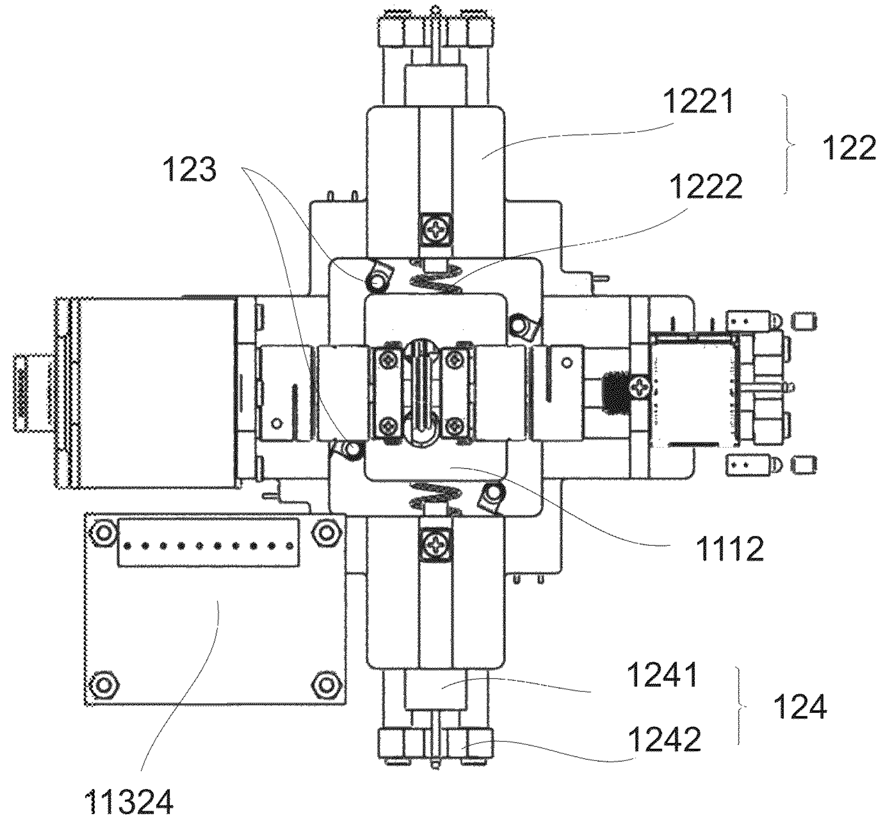
FIG. 13 is a bottom view illustrating an attitude adjustment part according to some embodiments of the present disclosure.

In some embodiments, the force feedback component 1132 may further include a motor control unit 11324 (as shown in FIG. 13). The motor control unit 11324 may be electrically connected to the signal transmission part and the actuator motor 11321. The motor control unit 11324 may control the movement of the actuator motor 11321 to achieve stable and accurate feedback of information on the needle insertion resistance. The motor control unit 11324 may include a motor drive part and a motor motion feedback part. The motor drive part may control a movement of the actuator motor 11321, i.e., a torque output mode. The motor motion feedback part may include, but is not limited to, position and speed information fed back by an encoder, and real-time current controlled by the actuator motor 11321 detected by a current detection unit, so as to control the actuator motor 11321. The motor motion feedback part is configured to convert a received force signal at the end of the robotic arm into an input signal of the motor drive part, so that the motor drive part may drive the actuator motor. In some embodiments, the motor control unit 11324 may be a motor driver.

Referring to FIG. 9, the mounting component 1131 may include a mounting base 11311 and a fixing base 11312 disposed on the mounting base 11311. The mounting base 11311 and the fixing base 11312 may be enclosed to form a mounting cavity for installing the second roller 11222. The actuator motor 11321 may be fixed on the mounting base 11311. The position detection unit 11322 may protrude from the mounting base 11311. The fixing base 11312 may be configured to install the handle housing 111.

The fixing base 11312 may be installed above the mounting base 11311. The handle housing 111 may be installed on the fixing base 11312, thereby fixing the handle housing 111. The actuator motor 11321 may be fixed on an end of the mounting base 11311. An output end of the actuator motor 11321 may extend into the mounting base 11311 and be connected to the second roller 11222 through the coupling 11323. A shaft end of the second roller 11222 away from the actuator motor 11321 may protrude from the mounting base 11311 and be provided with the position detection unit 11322. In some embodiments, the mounting component 1131 may further include a bearing through which the shaft end of the second roller 11222 is supported to ensure that the second roller 11222 rotates smoothly and avoids interference with the mounting base 11311 and the fixing base 11312.

When the master manipulator 100 controls the insertion of the puncture needle, the doctor may trigger the enabling trigger key 11231, the puncture enabling component 1123 may send a puncture enabling signal to the robot host through the signal transmission part, and then the robot host may control the end of the robotic arm to drive the puncture needle to prepare for the puncture operation. In this case, the doctor may move the slip ring 11211 along the handle shell 1111, so that the slip ring 11211 may move from a direction of the first roller 11221 to a direction of the second roller 11222. During the movement of the slip ring 11211, the slip ring 11211 may drive the connecting rope 11223 to move through the slide block 11212, and then the connecting rope 11223 may drive the first roller 11221 and the second roller 11222 to rotate. When the second roller 11222 rotates, the position detection unit 11322 on the second roller 11222 may detect a movement of the linear motion of the slip ring 11211, convert the movement into a rotational variable, and transmit the rotational variable to the robot host through the signal transmission part. The robot host may convert the rotational variable into a linear displacement of the puncture needle during puncturing. The robot host may control the movement of the end of the robotic arm according to the linear displacement of the puncture needle, so that the end of the robotic arm may perform the puncture operation, and finally the puncture needle may insert into the target puncture point.

While the puncture needle inserts into the patient's body, the sensor at the end of the robotic arm may detect a force generated by an interaction between the puncture needle and the human tissue, which is the needle insertion resistance of the puncture needle. The sensor may feedback the needle insertion resistance to the motor control unit 11324 through the robot host via the signal transmission part, the motor control unit 11324 may control the actuator motor 11321 to apply a certain current to generate a torque to act on the second roller 11222, then the torque of the second roller 11222 may apply the resistance to the connecting rope 11223, and then transmit the resistance to the slip ring 11211 through the connecting rope 11223 and then apply the resistance to the hands of the doctor. The doctor may feel the movement resistance, thereby realizing the feedback function of the puncture force.

In some embodiments, the puncture component 110 may not only realize the function of the puncture force feedback through the force feedback component 1132, but also realize the puncture force feedback through other methods. For example, the puncture component 110 may be connected with an air cylinder, and the puncture force feedback may be realized by changing an air pressure value in the air cylinder.

Figure 10:
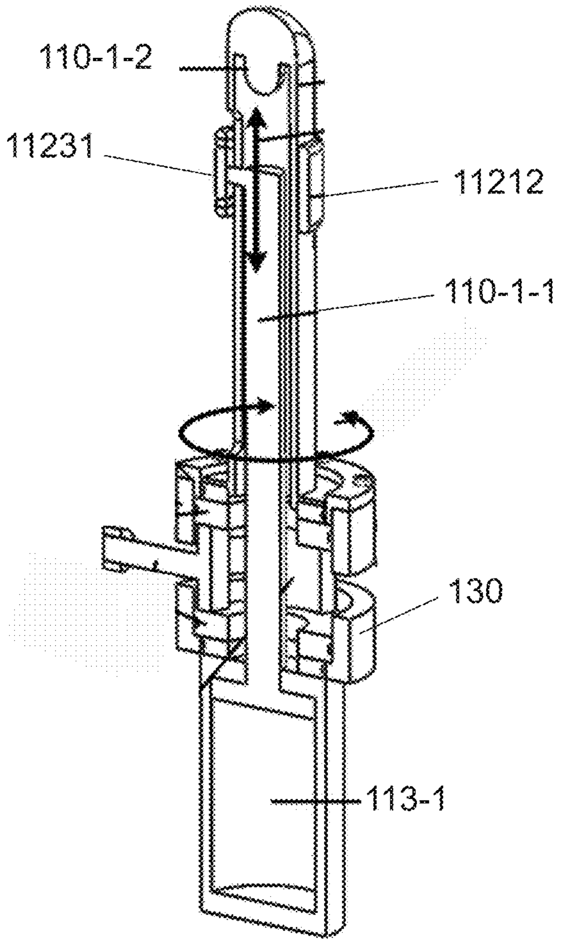
FIG. 10 is a structural diagram illustrating an exemplary puncture component according to some embodiments of the present disclosure.

FIG. 10 is a structural diagram illustrating an exemplary puncture component according to some embodiments of the present disclosure.

Referring to FIG. 10, in some embodiments, the puncture component 110 may include a push rod 110-1-1 slidably located in the handle housing 111 and fixedly connected to the slide block 11212. The enabling trigger key 11231 may be triggered, and a vertical movement of the slide block 11212 on the handle housing 111 may be realized by holding the slide block 11212, thereby driving the push rod 110-1-1 to move up and down on the handle housing 111. For example, when the puncture component 110 performs the puncture operation, the slide block 11212 may drive the push rod 110-1-1 to move down the handle housing 111 until the puncture needle at the end of the robotic arm enters the target puncture point.

The force feedback mechanism 113 may include an air cylinder 113-1 located at a bottom of the base 130. The push rod 110-1-1 may penetrate through the base 130 to be connected to the air cylinder 113-1. The air cylinder 113-1 is configured to convert the puncture force at the end of the robotic arm into a change of an air pressure to realize the force feedback. The base 130 may be provided with a through hole, and the push rod 110-1-1 may penetrate through the through hole to be connected to the air cylinder 113-1. The push rod 110-1-1 may move up and down along an extension direction of a spindle of a hollow columnar structure of the puncture component 110 in the through hole. When the puncture component 110 performs the puncture operation, the push rod 110-1-1 may be driven by the slide block 11212 to move down along the extension direction of the spindle. The push rod 110-1-1 may apply a force to the air cylinder 113-1 during the downward movement, and the air pressure value in the air cylinder 113-1 may change at this time. The change of the air pressure in the air cylinder 113-1 may be adjusted in real time through an external adjustment device, so that the air pressure value may correspond to the puncture force at the end of the robotic arm, thereby realizing the function of the puncture force feedback.

The puncture component 110 may further include a displacement sensor 110-1-2 which may be located at an end of the puncture component 110 and electrically connected to the communication device. The displacement sensor 110-1-2 may be configured to detect a sliding distance of the slide block 11212 sliding along the handle housing 111. Optionally, the displacement sensor 110-1-2 may be a laser displacement sensor. The laser displacement sensor may detect the sliding distance of the slide block 11212 sliding along the handle housing 111 and feedback a distance value to the puncture needle at the end of the robotic arm in real time, so that the puncture needle may perform a synchronous puncture movement.

In some embodiments, the piercing component 110 may also realize the needle insertion control on the end of the robotic arm through a screw nut mechanism, and realize the force feedback of the needle insertion resistance by using a depth feedback component.

Figure 11:
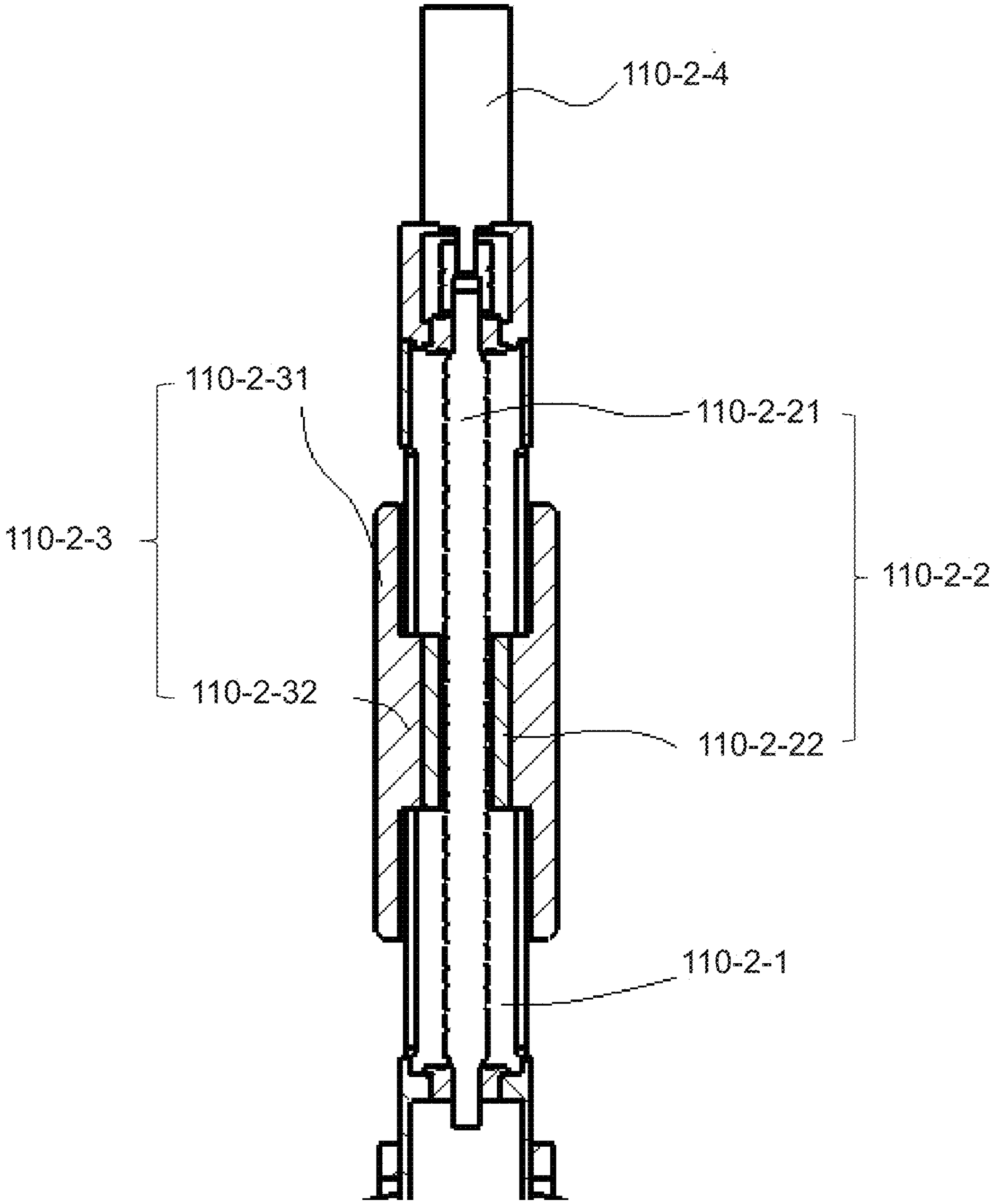
FIG. 11 is a structural diagram illustrating an exemplary puncture component according to some embodiments of the present disclosure.

FIG. 11 is a structural diagram illustrating an exemplary puncture component according to some embodiments of the present disclosure.

In some embodiments, referring to FIG. 11, the puncture component 110 may include a connecting rod 110-2-1, a handle 110-2-3, and a depth feedback component. One end of the connecting rod 110-2-1 may be movably connected to the base 130. The handle 110-2-3 may be slidably connected to the connecting rod 110-2-1. The depth feedback component may be electrically connected to the communication device for force feedback and needle insertion control of the handle 110-2-3 for depth adjustment.

In some embodiments, the puncture component 110 may further include a hinge part located at one end of the connecting rod 110-2-1. Another end of the connecting rod 110-2-1 may be disposed away from the base 130. The connecting rod 110-2-1 may rotate on a mounting end surface of the base 130 with the hinge part as a center of rotation. In this embodiment, the hinge part may be located at a lower end of the connecting rod 110-2-1; the connecting rod 110-2-1 may be hinged to the mounting end surface of the base 130 through the hinge part. In some embodiments, the hinge part may be a universal joint. In other embodiments, the hinge part may be a spherical hinge part. The handle 110-2-3 may be slidably mounted on the connecting rod 110-2-1 along an axial direction of the connecting rod 110-2-1.

In some embodiments, the handle 110-2-3 may be ring-shaped. The handle 110-2-3 may include a sliding sleeve 110-2-31 slidably sleeving an outer side of the connecting rod 110-2. Two ends of an inner side of the sliding sleeve 110-2-31 may form limiting protrusions 110-2-32 along the axial direction of the connecting rod 110-2-1. Sidewalls of the connecting rod 110-2-1 may form limiting grooves along the axial direction of the connecting rod 110-2-1. The limiting protrusions 110-2-32 may be movably arranged in the limiting grooves. The limiting grooves can effectively limit the sliding distance of the handle 110-2-3 when realizing sliding and guiding of the handle 110-2-3.

The handle 110-2-3 may rotate along the hinge part under an external force to achieve attitude adjustment or slide along the connecting rod 110-2-1 to achieve depth adjustment. Specifically, when the handle 110-2-3 rotates along the hinge part under the external force, an adjustment of an angle and a position when the needle is actually held can be effectively simulated; and when the handle 110-2-3 slides along the connecting rod 110-2-1 under the external force, the puncture action when the needle is actually held can be effectively simulated.

In some embodiments, the puncture component 110 may further include a screw nut mechanism 110-2-2. The screw nut mechanism 110-2-2 may include a screw rod 110-2-21 and a nut 110-2-22. The screw rod 110-2-21 may be rotatably installed inside the connecting rod 110-2-1, and a rotation axis of the screw rod 110-2-21 may coincide with an axis of the connecting rod 110-2-1. The nut 110-2-22 may be movably threadedly connected to the screw rod 110-2-21. The handle 110-2-3 may be fixedly connected to the nut 110-2-22. When the handle 110-2-3 drives the nut 110-2-22 to slide along the axis of the connecting rod 110-2-1, the screw rod 110-2-21 may rotate. The depth feedback component may be configured to generate an adjustable resistance opposite to a rotation direction of the screw rod 110-2-21.

A fixed connection between the handle 110-2-3 and the nut 110-2-22 may be as follows: an accommodating cavity may be formed in the sliding sleeve 110-2-31, and the nut 110-2-22 may be fixedly embedded in the accommodating cavity.

Due to the existence of the above-mentioned structure, the handle 110-2-3 may pressed by the external force, so that the nut 110-2-22 may move downward and thread-fit with the screw rod 110-2-21. The screw rod 110-2-21 may be driven by the nut 110-2-22 to rotate, and the rotation direction of the screw rod 110-2-21 may be determined by a movement direction of the nut 110-2-22.

In some embodiments, the depth feedback component may include a depth feedback motor 110-2-4. One end of the screw rod 110-2-21 may be coaxially and fixedly mounted on an output shaft of the depth feedback motor 110-2-4. The depth feedback motor 110-2-4 may transmit a puncture action of the handle 110-2-3 to the end of the robotic arm through a rotation angle change of the depth feedback motor 110-2-4, and adjust a rotation speed of the depth feedback motor 110-2-4 according to a contact force on the end of the robotic arm to realize the force feedback.

The depth adjustment action of the handle 110-2-3 may be converted into the rotation of the screw rod 110-2-21 through the screw nut mechanism 110-2-2. Because the screw rod 110-2-21 is coaxially and fixedly mounted on the output shaft of the depth feedback motor 110-2-4, the rotation of the screw rod 110-2-21 may drive the output shaft of the depth feedback motor 110-2-4 to have a rotation tendency. When a stator of the depth feedback motor 110-2-4 is powered on, an electromagnetic action between the stator and the rotor may exert a rotating electromagnetic force to the stator for driving the output shaft of the depth feedback motor 110-2-4 to have another rotation tendency, thereby forming a resistance hindering the rotation of the screw rod 110-2-21. The depth feedback motor 110-2-4 may be configured as that a magnitude of stator current is related to a magnitude of the contact force received from deep puncturing of an operator, thereby realizing the adjustable resistance.

When the master manipulator 100 is in use, the doctor may hold the handle 110-2-3 with the hand. When the doctor pushes the handle 110-2-3, the handle 110-2-3 may drive the connecting rod 110-2-1 to rotate with the hinge part as the center of rotation, thereby achieving attitude adjustment, and effectively simulating the adjustment of the angle and the position when the needle is actually held. When the doctor slides and presses the handle 110-2-3 on the connecting rod 110-2-1, the depth adjustment may be realized, thereby effectively simulating the puncture action when the needle is actually held. The depth feedback motor 110-2-4 may help the doctor transmit the corresponding adjustment action of the handle 110-2-3 to the end of the robotic arm and feedback the contact force with the object when the end of the robotic arm performs the corresponding adjustment action, to provide the doctor with a more realistic feeling of the puncture operation when simulating the actual needle holding, improve the success rate of the operation, and ensure the safety of patients.

Figure 12:
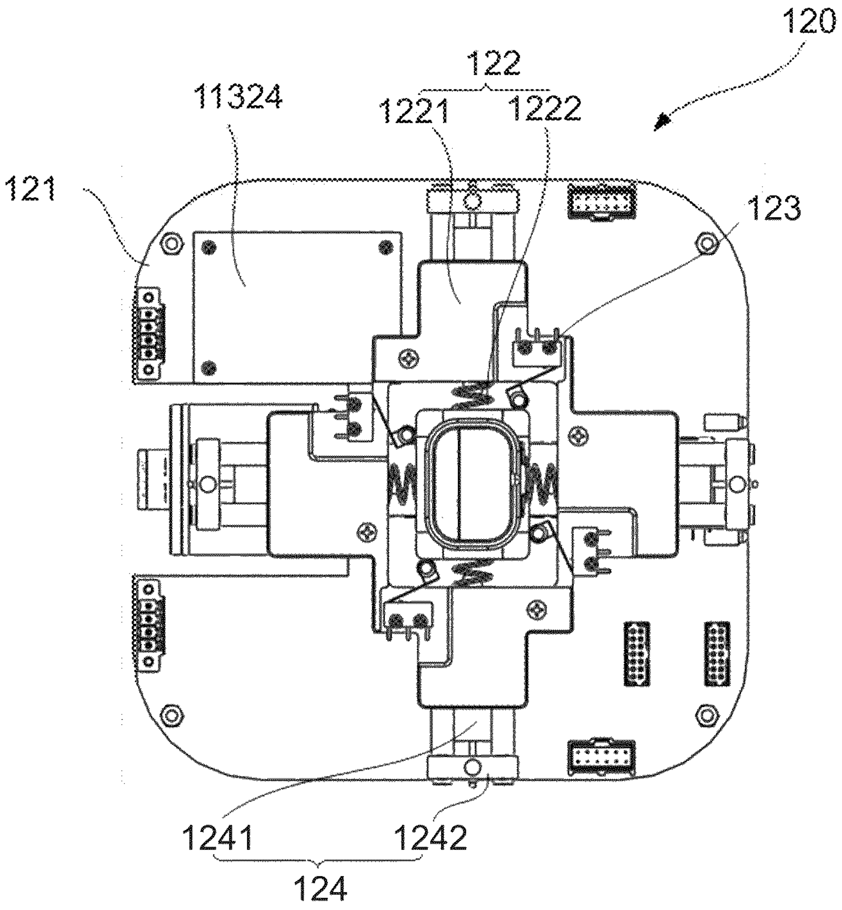
FIG. 12 is a top view illustrating an attitude adjustment part according to some embodiments of the present disclosure.

FIG. 12 is a top view illustrating an attitude adjustment part according to some embodiments of the present disclosure. FIG. 13 is a bottom view illustrating an attitude adjustment part according to some embodiments of the present disclosure.

Referring to FIG. 12 and FIG. 13, in some embodiments, the attitude adjustment part 120 may include an attitude adjustment housing 121 and a support mechanism 122 disposed in the attitude adjustment housing 121.

The attitude adjustment housing 121 may be a shell of the attitude adjustment part 120, and configured to install each part of the attitude adjustment part 120. The mounting base 1112 of the handle housing 111 may be rotatably installed in the attitude adjustment housing 121. The handle shell 1111 of the handle housing 111 may be connected to the mounting base 1112 in the attitude adjustment housing 121. In some embodiments, the attitude adjustment housing 121 may be provided with a spherical hinge. The mounting base 1112 may be arranged on the spherical hinge. The handle shell 1111 may drive the mounting base 1112 to rotate with respect to the attitude adjustment housing 121 through the spherical hinge, to realize the adjustment of the angle of the puncture component 110, realize the adjustment of a spatial attitude of the puncture needle, and make the puncture needle be aligned with the target puncture point.

The support mechanism 122 may be disposed in the attitude adjustment housing 121 and configured to support the handle housing 111. The mounting base 1112 of the handle housing 111 may be rotatably disposed on the support mechanism 122. When the handle housing 111 is not rotated, the support mechanism 122 may support the handle housing 111 to prevent the handle housing 111 from tilting and affecting the spatial attitude of the puncture needle.

In some embodiments, the attitude adjustment part 120 may further include an attitude adjustment force feedback component (not shown in the figure). The attitude adjustment force feedback component may apply a resistance to the attitude adjustment part 120 based on the attitude adjustment force feedback information. For example, the attitude adjustment force feedback component may feedback the resistance of the puncture needle during rotational attitude adjustment, to simulate the actual attitude adjustment process of the puncture needle and facilitate operation for the doctor. In some embodiments, the attitude adjustment force feedback component may be in communication connection to the robot host through the signal transmission part to realize information interaction. In some embodiments, when the attitude adjustment part 120 may drive the puncture needle to rotate to adjust the spatial attitude of the puncture needle, the puncture needle may encounter the attitude adjustment resistance, which may be fed back to the robot host, and the robot host may control the attitude adjustment force feedback component to apply a resistance equivalent to the attitude adjustment resistance at the end of the robotic arm to the attitude adjustment part 120. In this way, when the doctor drives the attitude adjustment part 120 to rotate, the doctor may feel the resistance opposite to the rotation direction, thereby realizing the force feedback during attitude adjustment. In some embodiments, the attitude adjustment force feedback component may include an attitude adjustment force feedback motor. The attitude adjustment force feedback motor may be mounted on a rotating shaft of the attitude adjustment part 120, and may also be mounted at another position (e.g., the base 130). Resistance may be applied to the rotating shaft through the attitude adjustment force feedback motor to simulate the resistance at the end of the robotic arm during attitude adjustment.

In some embodiments, the attitude adjustment part 120 may include a plurality of attitude adjustment trigger switches 123 arranged along a peripheral side of the puncture component 110. One end of the handle housing 111 may be rotatably installed in the support mechanism 122. The plurality of attitude adjustment trigger switches 123 may be arranged along the peripheral side of the handle housing 111. The attitude adjustment trigger switches 123 may be components for triggering the attitude adjustment action. For example, when the handle housing 111 triggers (e.g., presses) the attitude adjustment trigger switches 123, the attitude adjustment trigger switches 123 may send an attitude adjustment control signal to the attitude adjustment part 120, and the attitude adjustment action may start.

The attitude adjustment part 120 may also include a plurality of inclination detectors (not shown) arranged along a peripheral side of the puncture component 110. The plurality of inclination detectors may detect an inclination of the puncture component 110 and transmit the inclination of the puncture component 110 to the communication device. The plurality of inclination detectors may respectively detect an inclination of the handle housing 111. The plurality of inclination detectors may be disposed on the support mechanism 122 and surround the handle housing 111. When the handle housing 111 is inclined towards a certain direction, the inclination detector corresponding to the direction may detect the inclination of the handle housing 111, and then detect the inclination angle of the handle housing 111. The inclination detectors may be electrically connected to the signal transmission part. The inclination detectors may feedback the inclination of the handle housing 111 to the robot host through the signal transmission part. The robot host may control the movement of the end of the robotic arm according to the inclination to adjust the spatial attitude of the puncture needle on the end of the robotic arm, thereby making the puncture needle aligned with the target puncture point.

When the handle housing 111 is inclined, the handle housing 111 may not correspond to any inclination detector, but correspond to a position between two inclination detectors. In this case, the two inclination detectors may jointly detect the inclination of the handle housing 111. The principle of jointly detecting the inclination of the handle housing 111 by two inclination detectors is substantially the same as that of one inclination detector, which is not repeated here.

Merely by way of example, there may be four attitude adjustment trigger switches 123 and/or the inclination detectors, the support mechanism 122 may have an avoidance space for installing the attitude adjustment trigger switches 123 and/or the inclination detectors, and the four attitude adjustment trigger switches 123 and/or the inclination detectors may be evenly distributed on the peripheral side of the handle housing 111.

In some embodiments, the attitude adjustment housing 121 may include a bearing base and an attitude adjustment shell covering the bearing base. The attitude adjustment shell and an attitude adjustment base may be enclosed to form a cavity, and the support mechanism 122 and the attitude adjustment trigger switches 123 may be arranged in the cavity.

In some embodiments, the support mechanism 122 may include a support frame 1221 and a plurality of support elastic members 1222. The support frame 1221 is provided with a mounting space for installing the mounting base 1112. The mounting base 1112 may be located in the mounting space. The plurality of support elastic members 1222 may surround a peripheral side of the mounting base 1112 and may connect the support frame 1221 and the mounting base 1112.

The support frame 1221 may be arranged on the bearing base of the attitude adjustment housing 121. The mounting space may be arranged in a middle region of the support frame 1221. The mounting base 1112 may be rotatably installed in the mounting space of the support frame 1221 through the spherical hinge. That is to say, a movement relationship between the attitude adjustment part 120 and the puncture component 110 may be established through the support frame 1221, so that the puncture component 110 may move relative to the handle structure. Moreover, there may be a certain space between an inner wall of the mounting space and the mounting seat 1112, which facilitates the rotation of the handle housing 111 and avoids interference between the handle housing 111 and the support frame 1221.

The support elastic members 1222 may be elastically connected to the mounting base 1112 and the support frame 1221, and the support elastic members 1222 may support the mounting base 1112, to limit the automatic rotation of the handle housing 111 without external force. The plurality of support elastic members 1222 may surround the peripheral side of the mounting base 1112 to ensure that the handle housing 111 maintains a balanced state. Exemplarily, there may be four support elastic members 1222 evenly distributed on the peripheral side of the mounting base 1112. In some embodiments, the support elastic members 1222 may be springs.

When the attitude adjustment action is performed, the doctor may control the slip ring 11211 or another position of the handle housing 1111, and then swing the handle housing 111. When the mounting base 1112 triggers any attitude adjustment trigger switch 123 on the peripheral side, the handle housing 111 may swing along an axial direction (intra-layer) of actuator motor 11321 and a vertical direction (inter-layer) of the actuator motor 11321. When the handle housing 111 is in contact with and triggers any one of the four attitude adjustment trigger switches 123 on the peripheral side, the end of the robotic arm may be driven to adjust the attitude of the puncture needle along this direction.

Two of the four attitude adjustment trigger switches 123 may be arranged along the axial direction of the actuator motor 11321, and the other two of the four attitude adjustment trigger switches may be arranged along a direction perpendicular to the axial direction of the actuator motor 11321. That is to say, two of the attitude adjustment trigger switches 123 may be arranged in positive and negative directions (intra-layer) along the axial direction of the actuator motor 11321, and the other two of the attitude adjustment trigger switches 123 may be arranged in positive and negative directions (inter-layer) along the direction perpendicular to the axial direction of the actuator motor 11321. In this way, when the handle housing 111 rotates, the puncture needle may be driven to rotate in any direction of the intra-layer positive and negative directions and the inter-layer positive and negative directions, to adjust the spatial attitude of the puncture needle.

In some embodiments, when the handle housing 111 triggers the attitude adjustment trigger switches 123 to perform the attitude adjustment action, the inclination detectors may feedback the inclination of the handle housing 111 to the robot host through the signal transmission part, and drive the end of the robotic arm to rotate along a direction of the inclination of the handle housing 111 through the robot host to adjust the spatial attitude of the puncture needle. The handle housing 111 may continuously trigger the four attitude adjustment trigger switches 123 to adjust the spatial attitude of the puncture needle, so that an insertion direction of the puncture needle may coincide with the target puncture point, and then perform the puncture action to complete the puncture operation.

In some embodiments, the attitude adjustment part 120 may further include a locking mechanism 124 disposed on the attitude adjustment housing 121 for locking or unlocking the handle housing 111. When the locking mechanism 124 performs unlocking, the handle housing 111 may rotate with respect to the attitude adjustment housing 121. The locking mechanism 124 may realize locking and unlocking of the mounting base 1112. The locking mechanism 124 may be disposed in the attitude adjustment housing 121, and the locking mechanism 124 may be contacted with or separated from the mounting base 1112.

When the locking mechanism 124 locks the mounting base 1112, the locking mechanism 124 may be contacted with the mounting base 1112, and the mounting base 1112 may not rotate with respect to the support frame 1221. In this case, the handle housing 111 may not rotate, and then the spatial attitude of the puncture needle may not be adjusted. When the spatial attitude of the puncture needle needs to be adjusted, the locking mechanism 124 may unlock the mounting base 1112, so that the locking mechanism 124 may be separated from the mounting base 1112. In this case, the mounting base 1112 may rotate with respect to the support frame 1221. During rotation, the handle housing 111 may incline against the elastic force of the support elastic members 1222 to adjust the spatial attitude of the puncture needle.

When the puncture needle is aligned with the target puncture point, the locking mechanism 124 may lock the mounting base 1112, so that the spatial attitude of the puncture needle does not change anymore, preventing the rotation of the handle housing 1111 with respect to the support frame 1221 from affecting the spatial attitude of the puncture needle. Then, the puncture component 110 may control the puncture needle to perform the needle insertion operation.

In some embodiments, the locking mechanism 124 may include a plurality of electromagnets 1241 and a plurality of state detection units 1242 corresponding to the plurality of electromagnets 1241. The electromagnets 1241 may be arranged on the support frame 1221 and surround the peripheral side of the mounting base 1112. When the electromagnets 1241 are powered off, extension shafts may abut against the mounting base 1112 to limit the rotation of the mounting base 1112. The state detection units 1242 may be configured to detect working states of the electromagnets 1241.

The electromagnets 1241 may be provided with the extension shafts. When the electromagnets 1241 are powered off, the extension shafts of the electromagnets 1241 may remain extended to contact the mounting base 1112 to limit the rotation of the mounting base 1112 toward the extension shafts. When the electromagnets 1241 are powered of, the extension shafts of the electromagnets 1241 may retract, and ends of the extension shafts may be separated from the mounting base 1112. In this case, the restraint of the mounting base 1112 toward the direction of the extension shafts may be released, and the mounting base 1112 may move toward the direction of the extension shafts.

In some embodiments, there may be a plurality of electromagnets 1241 evenly distributed along a circumference of the mounting base 1112. The mounting base 1112 may be locked by the plurality of electromagnets 1241 to ensure reliable locking of the mounting base 1112. Exemplarily, there may be four electromagnets 1241 evenly distributed on the peripheral side of the mounting base 1112. When the four electromagnets 1241 extend, the mounting base 1112 may be locked. In some embodiments, the electromagnets 1241 may be fixed on the support frame 1221 by threads or other components. The support elastic members 1222 may keep the handle housing 111 in a vertical state in the retracted state of the electromagnets 1241 and provide a restoring force of movement for an attitude adjustment.

The state detection units 1242 may detect the working states of the electromagnets 1241 in real time, and feedback the working states of the electromagnets 1241 to the signal transmission part. The state detection units 1242 may detect whether the electromagnets 1241 are working normally, thereby improving the safety of the whole machine. When the electromagnets 1241 are powered off, the state detection units 1242 may detect that the electromagnets 1241 lock the mounting base 1112. In this case, the state detection units 1242 may feedback a signal representing that the mounting base 1112 is locked to the signal transmission part, indicating that the handle housing 111 cannot rotate. When the electromagnets 1241 are powered on, the state detection units 1242 may detect that the electromagnets 1241 unlock the mounting base 1112. In this case, the state detection units 1242 may feedback a signal representing that the mounting base is unlocked 1112 to the signal transmission part, indicating that the handle housing 111 can rotate. In some embodiments, the state detection units 1242 may be photoelectric switches, or other components capable of detecting the states of the electromagnets 1241.

In some embodiments, the locking mechanism 124 may also include an attitude adjustment switch disposed on the attitude adjustment housing 121. The attitude adjustment switch may be electrically connected to the electromagnets 1241. The attitude adjustment switch may control the power on/off of the electromagnets 1241. The attitude adjustment switch may be electrically connected to the signal transmission part. The attitude adjustment switch may be located on an upper surface of the attitude adjustment housing 121.

When the attitude adjustment switch is operated, the attitude adjustment switch may control the electromagnets 1241 to be powered on, so that the extension shafts of the electromagnets 1241 may be separated from the mounting base 1112, the mounting base 1112 may be unlocked, and the mounting base 1112 may rotate with respect to the support frame. When the attitude adjustment switch is operated again, the attitude adjustment switch may control the electromagnets 1241 to be powered off, and the extension shafts of the electromagnets 1241 may extend to lock the mounting base 1112 under the action of the springs. The locking and unlocking control of the mounting base 1112 may be realized by powering on/off the electromagnets 1241.

Before the attitude adjustment action is performed, the electromagnets 1241 may be unlocked through the attitude adjustment switch to control the extension shafts of the electromagnets 1241 to retract from the mounting base 1112 of the puncture component 110. In this case, the mounting base 1112 may move to realize the adjustment of the spatial attitude of the puncture needle. When the extension shafts are contacted with the mounting base 1112, the handle housing 111 cannot rotate, thereby avoiding falsely triggering the attitude adjustment action when the puncture action is performed. Moreover, due to clinical requirements, the handle housing 111 cannot rotate during the puncture process to ensure the stability of the puncture process and the puncture effect. Therefore, before the puncture action is performed, the attitude adjustment action may be performed. After the attitude adjustment action is completed, the handle housing 111 may be locked by the attitude adjustment switch, and finally, the puncture action may be performed. In some embodiments, the attitude adjustment action and the puncture action may also be performed in turn, as long as the extension shafts of the electromagnets 1241 are retracted before the attitude adjustment action is performed, and the extension shafts of the electromagnets 1241 extend before the puncture action is performed.

Figure 14:
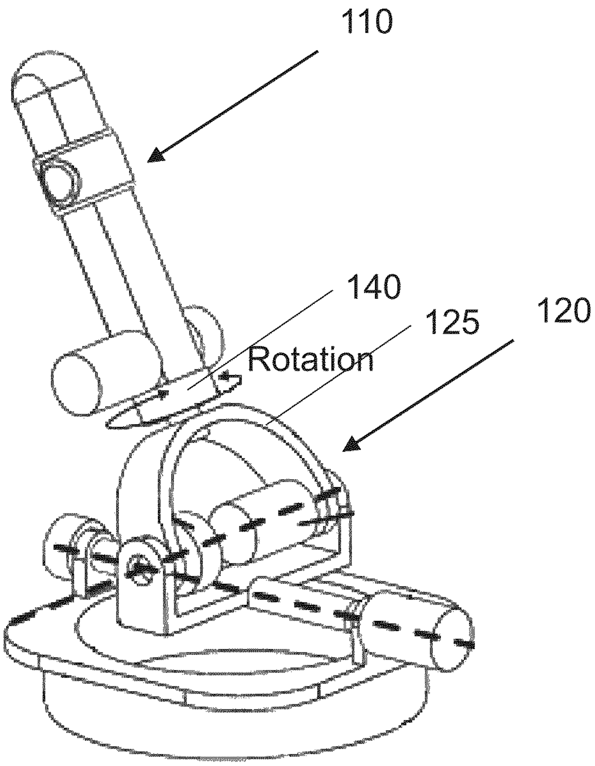
FIG. 14 is a diagram illustrating an exemplary structure of another state of a master manipulator according to some embodiments of the present disclosure.

FIG. 14 is a structural diagram illustrating another state structure of a master manipulator according to some embodiments of the present disclosure.

Referring to FIG. 14, in some embodiments, the puncture component 110 may be a hollow columnar structure, the puncture component 110 may rotate along a spindle of the hollow columnar structure, and the puncture component 110 may be rotatably connected to the attitude adjustment part 120. A spindle direction of the puncture component 110 may be a length direction of the puncture component 110.

The puncture component 110 may be configured to control the needle insertion of the puncture needle at the end of the robotic arm of the robot. The puncture component 110 may be rotatably connected to the attitude adjustment part 120. The puncture component 110 may rotate around an axis (i.e., the spindle of the hollow cylindrical structure) of the puncture component 110, and the rotation of the puncture component 110 may not be synchronized to the robot. The puncture component 110 may freely rotate around the axis of the puncture component 110. When the puncture component 110 is operated, an operator's arm may be placed in a relatively comfortable attitude without affecting the corresponding relationship between attitude adjustment planes or attitude adjustment joints, thereby realizing absolute attitude adjustment and puncture action.

In some embodiments, the master manipulator 100 may include a handle rotation component 140 configured to rotatably mount the puncture component 110 on an adapter base 125 of the attitude adjustment part 120. The handle rotation component 140 may include a rotation bracket and a rotation bearing mounted between the rotation bracket and the puncture component 110, and the rotation bracket may be mounted on the attitude adjustment part 120; the rotation bearing may sleeve an end of the puncture component 110 relatively close to the attitude adjustment part 120, and the rotation bearing may be connected to the rotation bracket. The rotation bracket may be configured to bear the rotation bearing, and connect the rotation bearing to the adapter base 125 of the attitude adjustment part 120. The rotation bearing may be configured to rotatably mount the handle housing 111 of the puncture component 110 on the adapter base 125.

It can be understood that in other embodiments, the rotation bracket may be correspondingly omitted, as long as the puncture component 110 may be rotatably disposed on the adapter base 125.

In this embodiment, a rotational degree of freedom between the puncture component 110 and the attitude adjustment part 120 may make the operator manipulate the puncture component 110 in a more comfortable attitude.

Figure 15:
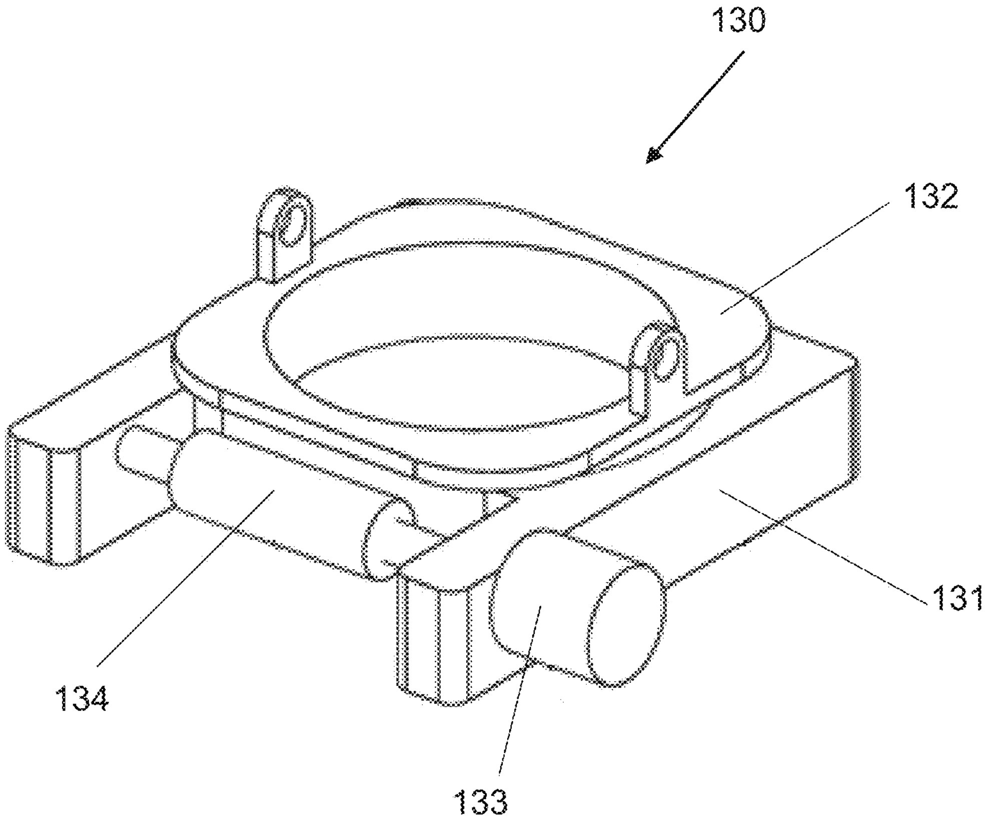
FIG. 15 is a structural diagram illustrating an exemplary base according to some embodiments of the present disclosure.

FIG. 15 is a structural diagram illustrating an exemplary base according to some embodiments of the present disclosure.

In some embodiments, referring to FIG. 15, the master manipulator 100 may further include a base 130. The base 130 may be arranged on a bottom of the attitude adjustment part 120 for supporting and bearing. The base 130 may include a base body 131 and a rotating platform 132. A degree of freedom for mapping a robot attitude may be added to the attitude adjustment part 120 by arranging the rotating platform 132, and the degree of freedom may map the attitude adjustment plane of a functional part at the end of the robotic arm, so that a one-to-one mapping relationship may be formed between the master manipulator 100 and the robot. The rotating platform 132 may be fixedly connected to the attitude adjustment part 120. The rotating platform 132 may be rotatably connected to the base body 131. The rotating platform 132 may be parallel to a plane where the base body 131 is located with respect to a rotating plane of the base body, and the rotating platform 132 may be related to at least one joint movement of the robot. In some embodiments, the rotating platform may not be parallel to the plane where the base body 131 is located with respect to the rotating plane of the base body 131, as long as the mapping relationship between the master manipulator 100 and at least one joint of the robot can be guaranteed.

In some embodiments, the base body 131 may be a frame structure, and a shape of the base body 131 may be a square, a circle, a polygon, etc., which is not limited here. A mounting space may be arranged in a middle of the base body 131. A size of the mounting space may correspond to a size of the rotating platform 132. The rotating platform 132 may be arranged in the mounting space of the base body 131 and rotatably connected to the base body 131. The attitude adjustment part 120 may be installed on the rotating platform 132.

In some embodiments, the base 130 may also include a driving member 133 and a transmission component. The driving member 133 may be a driving member such as a motor that adapts to the power required by the rotating platform 132. The driving member 133 may be directly connected to the rotating platform 132, and may also be connected to the rotating platform 132 through the transmission component to drive the rotating platform 132 to rotate. In some embodiments, the driving member 133 may be electrically connected to the signal transmission part, and communicate with the robot host through the communication device.

In some embodiments, the transmission component may include a worm 134 and a worm gear that mesh with each other. The worm 134 may be connected to an output end of the driving member 133, and the worm gear may be fixedly connected to the rotating platform 132. When the driving member 133 drives the worm 134 to rotate, the worm gear may rotate correspondingly with the rotation of the worm, and drive the rotating platform 132 to rotate around a perpendicular line of a plane where the rotating platform 132 is located; and the rotation of the rotating platform 132 may adjust an overall attitude orientation of the attitude adjustment part 120.

In some embodiments, the transmission component may include a driving wheel and a driven wheel. A synchronous belt may sleeve the driving wheel and the driven wheel. The driving wheel may be connected to an output end of the driving member, and the driven wheel may be fixedly connected to the rotating platform. When the driving member 133 drives the driving wheel to rotate, the driving wheel may drive the driven wheel to rotate through the synchronous belt, and drive the rotating platform 132 to rotate around the perpendicular line of the plane where the rotating platform 132 is located. In some embodiments, the transmission component may also be a gear, etc., as long as the transmission component may be connected to the driving member 133 and drive the rotating platform 132 to rotate.

In some embodiments, the rotating platform 132 may be provided with an encoder. The encoder may detect a rotation angle of the rotating platform 132 and transmit the rotation angle of the rotating platform 132 to the communication device. The encoder may be electrically connected to the signal transmission part, and the detected rotation angle may be transmitted to the robot host through the signal transmission part. The robot host may control an attitude adjustment plane corresponding to at least one joint of the robot to rotate at a same angle according to the rotation angle, thereby realizing a synchronous change of the rotating platform and the attitude adjustment plane. In some embodiments, the rotating platform 132 may be actively synchronized with the attitude adjustment plane where the at least one joint of the robot is located.

In some embodiments, the master manipulator 100 may further include an emergency stop switch and an integral switch. The emergency stop switch and the integral switch may be respectively electrically connected to the signal transmission part. The emergency stop switch may control the emergency stop of the master manipulator to avoid the inability to stop the operation when an accident occurs. The integral switch may be configured to realize an on/off operation of the master manipulator 100.

In some embodiments, the master manipulator 100 may further include state indication units and a plurality of indicator lights including but not limited to an indicator light of handle rotation, a movement indicator light of the slide block 11212, or the like. The state indication units are configured to control on/off of all the indicator lights. Taking the movement indicator light of the slide block 11212 as an example, when the movement indicator light of the slide block 11212 is in a flicker state, the signal transmission part may receive a signal of triggering a movement of the slip ring 11211. The motor control unit 11324 may output an equal amount of resistance acting on the hand according to the real-time force information sent by the robot host, thereby achieving the force feedback.

When the master manipulator 100 is in use, first the spatial attitude of the puncture needle may be adjusted through the attitude adjustment part 120, then the attitude adjustment part 120 may be locked, and then the puncture needle may be controlled to perform the needle insertion operation through the puncture component 110. After the puncture operation is completed, the puncture component 110 may control the puncture needle to perform the needle withdrawal operation. It is worth noting that the process of adjusting the spatial attitude of the puncture needle by the attitude adjustment part 120 and the puncture process of the puncture needle controlled by the puncture component 110 have been mentioned above, which are not repeated here.

In some embodiments, the master manipulator 100 may simulate the clinical puncture process through the puncture component 110 to perform the puncture function, and adjust the spatial attitude of the puncture needle at the end of the robotic arm through the attitude adjustment part 120, so that the needle insertion route of the puncture needle may coincide with the target puncture point. The master manipulator 100 may integrate the puncture function and the attitude adjustment function, and may complete all operations with one hand. Specifically, the master manipulator 100 may adopt a small-section handle housing 1111 with an external slip ring 11211 in structure, so that the attitude adjustment and the needle insertion operation of the puncture needle may be completed with two fingers on one hand without interference with the action structure, so that the operation is simple and intuitive, and easy to use.

Figure 16:
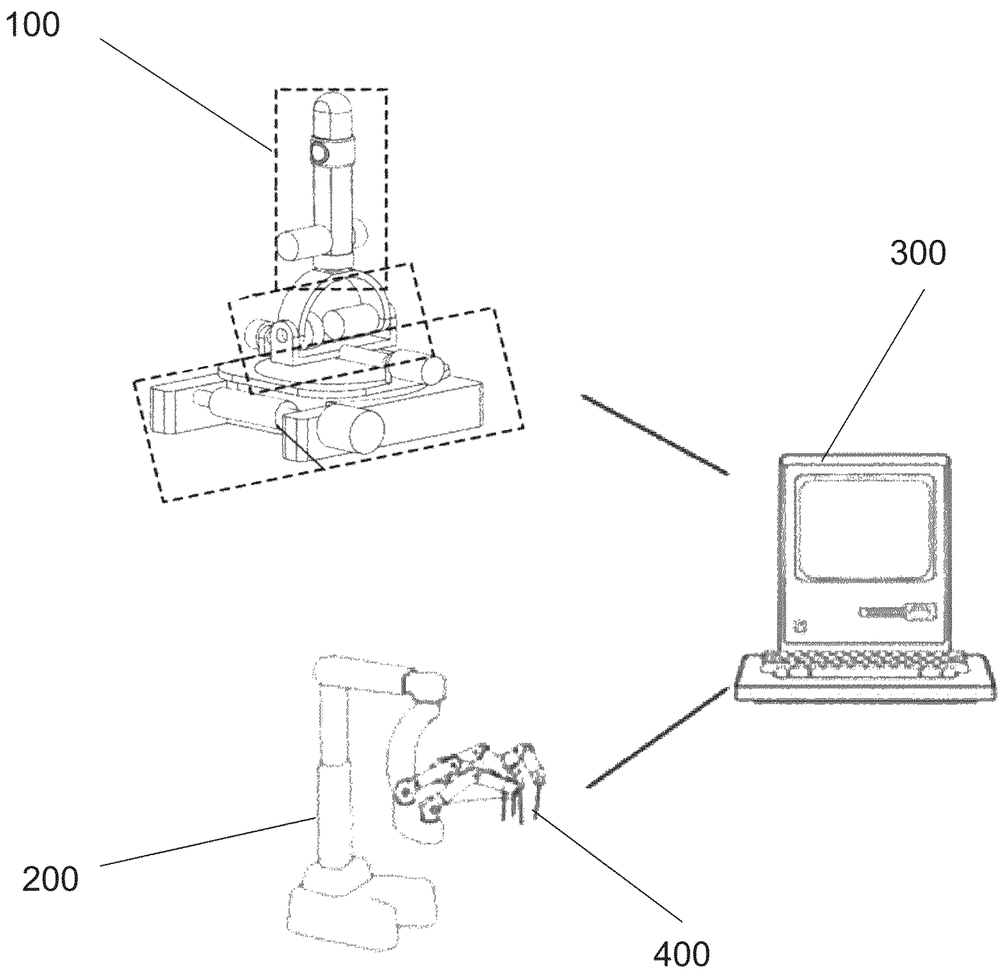
FIG. 16 is a diagram illustrating an exemplary system of a robot according to some embodiments of the present disclosure.

FIG. 16 is a system diagram illustrating an exemplary robot according to some embodiments of the present disclosure.

The present disclosure further provides a robot. Referring to FIG. 16, the robot may include a puncture needle 400 at an end of the robot and the master manipulator 100 of any of the embodiments. The puncture needle 400 may be disposed at the end of the robotic arm of the robot. The robot may be electrically connected to a communication device 300 and the puncture needle 400. The master manipulator 100 may be electrically connected to the end of the robotic arm and the puncture needle 400 through the communication device 300, and configured to control the end of the robotic arm to drive the puncture needle 400 to perform a puncture operation.

When the robot is actually used, a robot host 200 may be located in a scanning room. Optionally, the robot host 200 may be a robotic arm body and configured to drive the end of the robotic arm to move to adjust an attitude of the puncture needle at the end of the robotic arm. The end of the robotic arm may be arranged on the robot host 200 for performing a puncture action. A control room and the scanning room may be arranged adjacently or at intervals. An operating table of an imaging device may be arranged in the control room, and there may be a concrete wall between the control room and the scanning room to shield the radiation. Moreover, the master manipulator 100 may also installed in the control room. The doctor may control the robot host 200 in the scanning room by operating the master manipulator 100 in the control room, to complete the master-slave teleoperated puncture surgery.

The basic concept has been described above. Obviously, for those skilled in the art, the above detailed disclosure is only an example, and does not constitute a limitation to the present disclosure. Although not expressly stated here, those skilled in the art may make various modifications, improvements and corrections to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, "one embodiment," "an embodiment," and/or "some embodiments" refer to a certain feature, structure or characteristic related to at least one embodiment of the present disclosure. Therefore, it should be emphasized and noted that references to "one embodiment," or "an embodiment," or "an alternative embodiment" two or more times in different places in the present disclosure do not necessarily refer to the same embodiment. In addition, certain features, structures or characteristics in one or more embodiments of the present disclosure may be properly combined.

Furthermore, those having ordinary skills in the art will appreciate that aspects of the present disclosure may be illustrated and described in several patentable categories or circumstances, including any new and useful processes, machines, products, or a combination thereof, or any new and useful improvements thereto. Therefore, various aspects of the present disclosure may be fully implemented by hardware, may be fully implemented by software (including firmware, resident software, microcode, etc.), or may be implemented by a combination of hardware and software. The above hardware or software may be referred to as a "unit," "module," or "system". Furthermore, aspects of the present disclosure may take the form of a computer program product embodied in one or more computer-readable media, with computer-readable program code.

A computer readable signal medium may include a propagated data signal embodying computer program code, for example, in baseband or as part of a carrier. Such propagated signals may take many forms, including electromagnetic, optical, etc., or any suitable combination thereof. A computer-readable signal medium may be any computer-readable medium other than a computer-readable storage medium, which can communicate, propagate, or transfer the program for use by being connected to an instruction execution system, apparatus, or device. Program code on a computer readable signal medium may be transmitted over any suitable medium, including radio, electrical cable, optical fiber cable, RF, etc., or any combination of the foregoing.

The computer program codes required for the operation of each part of the application can be written in any one or more programming languages, including object-oriented programming languages, such as Java, Scala, Smalltalk, Eiffel, JADE, Emerald, C++, C#, VB.NET, Python, etc., conventional procedural programming languages, such as C programming language, Visual Basic, Fortran2103, Perl, COBOL2102, PHP, ABAP, etc., dynamic programming language or other programming languages such as Python, Ruby, Groovy, etc. The program code may run entirely on the user's computer, or as a stand-alone software package, or partly on the user's computer and partly on a remote computer, or entirely on the remote computer or server. In the latter case, the remote computer may be connected to the user computer through any type of network, including a local area network (LAN) or wide area network (WAN), or it can establish a connection with an external computer (e.g., by using an Internet service provider's network), or in a cloud computing environment or as a service, e.g., software as a service (SaaS).

In addition, unless clearly stated in the claims, the sequence of processing elements and sequences described in the present disclosure, the use of counts and letters, or the use of other names are not used to limit the sequence of processes and methods in the present disclosure. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, numbers describing the number of ingredients and attributes are used. It should be understood that such numbers used for the description of the embodiments use the modifier "about," "approximately," or "substantially" in some examples. Unless otherwise stated, "about," "approximately," or "substantially" indicates that the number is allowed to vary by ±20%. Correspondingly, in some embodiments, the numerical parameters used in the description and claims are approximate values, and the approximate values may be changed according to the required characteristics of individual embodiments. In some embodiments, the numerical parameters should consider the prescribed effective digits and adopt the method of general digit retention. Although the numerical ranges and parameters used to confirm the breadth of the range in some embodiments of the present disclosure are approximate values, in specific embodiments, settings of such numerical values are as accurate as possible within a feasible range.

For each patent, patent application, patent application publication, or other materials cited in the present disclosure, such as articles, books, specifications, publications, documents, or the like, the entire contents of which are hereby incorporated into the present disclosure as a reference. The application history documents that are inconsistent or conflict with the content of the present disclosure are excluded, and the documents that restrict the broadest scope of the claims of the present disclosure (currently or later attached to the present disclosure) are also excluded. It should be noted that if there is any inconsistency or conflict between the description, definition, and/or use of terms in the auxiliary materials of the present disclosure and the content of the present disclosure, the description, definition, and/or use of terms in the present disclosure is subject to the present disclosure.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A master manipulator of a robot, comprising:

a puncture component including a handle housing, a puncture actuator movably arranged on the handle housing, and a force feedback mechanism arranged at a bottom of the handle housing, the force feedback mechanism and the puncture actuator being connected, the force feedback mechanism applying resistance to the puncture component based on puncture force feedback information, and the puncture actuator including a sliding component, wherein the sliding component includes a slip ring and a slide block connected to the slip ring, and the slip ring sleeves an outer side of the handle housing; and an attitude adjustment part;

wherein the puncture actuator further includes a puncture enabling component disposed on the sliding component, and a linear motion component disposed inside the handle housing, wherein the sliding component is slidably arranged on the handle housing and connected to the linear motion component, the puncture enabling component is electrically connected to a communication device, and the puncture enabling component feeds back a puncture enabling signal to an end of a robotic arm through the communication device.

2. The master manipulator of claim 1, wherein the puncture enabling component includes an enabling trigger key arranged on the slip ring, and when the enabling trigger key is in a triggered state, the puncture enabling signal is fed back to the end of the robotic arm through the communication device.

3. The master manipulator of claim 2, wherein the puncture actuator includes a slide rail, the slide rail is arranged on an inner wall of the handle housing, the slip ring slidably sleeves the handle housing, the puncture enabling component is arranged in the slip ring and the handle housing, and the puncture enabling component is slidably connected to the slide rail.

4. The master manipulator of claim 3, wherein the puncture enabling component further includes a transmitting part and a receiving part arranged at both ends of the puncture component, the transmitting part emits a photoelectric signal, and the receiving part receives the photoelectric signal.

5. The master manipulator of claim 4, wherein the puncture enabling component further includes a shading block and a press reset key, the slide block is slidably arranged on the slide rail, the enabling trigger key is arranged on the slip ring in a pressable manner, the shading block is connected to the enabling trigger key, and the press reset key is elastically connected to the shading block and the slide block, and when the enabling trigger key is pressed, the shading block controls the puncture enabling component to transmit the puncture enabling signal to the end of the robotic arm by blocking the photoelectric signal.

6. The master manipulator of claim 3, wherein the puncture enabling component includes a puncture trigger switch and a contact wire, one end of the puncture trigger switch is connected to the enabling trigger key, another end of the puncture trigger switch is contacted with or separated from the contact wire, the contact wire is electrically connected to the communication device; and when the enabling trigger key is pressed, the puncture trigger switch is separated from the contact wire, and the contact wire transmits the puncture enabling signal to the end of the robotic arm through the communication device.

7. The master manipulator of claim 6, wherein the puncturing trigger switch is rotatably arranged on the handle housing, the puncture trigger switch has a rotation center located in a middle of the puncture trigger switch, and the puncture trigger switch rotates around the rotation center.

8. The master manipulator of claim 7, wherein the puncture enabling component includes the press reset key configured to reset the enabling trigger key, and the press reset key is arranged on the puncture trigger switch and a support part inside the handle housing.

9. The master manipulator of claim 1, wherein the linear motion component includes a first roller, a second roller spaced apart from the first roller, and a connecting rope connecting the first roller and the second roller, the slide block being connected to the connecting rope.

10. The master manipulator of claim 9, wherein the force feedback mechanism includes a mounting component and a force feedback component, the force feedback component is connected to the linear motion component, the mounting component is installed on a bottom of the handle housing and configured to install the force feedback component, the linear motion component is arranged on the handle housing and connected to the slide block, and the force feedback component applies resistance to the linear motion component.

11. The master manipulator of claim 10, wherein the first roller is rotatably arranged on an end of the handle housing away from the mounting component, the second roller is rotatably arranged on the mounting component, the puncture enabling component further includes a mounting base and a fixing part, the mounting base connects the slide block and the slip ring, and the connecting rope is fixed to the mounting base through the fixing part.

12. The master manipulator of claim 11, wherein the force feedback component includes an actuator motor and a position detection unit, the actuator motor and the position detection unit are respectively arranged on an axial end of the second roller, the position detection unit detects a movement of the slip ring and transmits the movement of the slip ring to the communication device, the actuator motor converts a puncture force fed back from the end of the robotic arm into a torque, and the torque is applied to the connecting rope.

13. The master manipulator of claim 1, wherein the puncture component includes a push rod slidably located in the handle housing and fixedly connected to the slide block.

14. The master manipulator of claim 13, wherein the force feedback mechanism includes an air cylinder located at a bottom of a base, the push rod penetrates through the base to be connected to the air cylinder, and the air cylinder converts puncture force at the end of the robotic arm into a change of an air pressure value.

15. The master manipulator of claim 13, wherein the puncture component includes a displacement sensor located at an end of the puncture component, and the displacement sensor detects a sliding distance of the slide block sliding along the handle housing and transmits the sliding distance of the slide block to the communication device.

16. The master manipulator of claim 1, wherein the puncture component is a hollow columnar structure, the puncture component rotates along a spindle of the hollow columnar structure, and the puncture component is rotatably connected to the attitude adjustment part.

17. The master manipulator of claim 16, wherein the master manipulator includes a handle rotation component including a rotation bracket and a rotation bearing mounted between the rotation bracket and the puncture component, the rotation bracket is mounted on the attitude adjustment part, and the rotation bearing sleeves an end of the puncture component relatively close to the attitude adjustment part.

18. A robot, comprising a puncture needle at an end of the robot and a master manipulator wherein the puncture needle is arranged at an end of a robotic arm of the robot, the robot is electrically connected to a communication device, and the master manipulator is electrically connected to the communication device and the puncture needle, and the master manipulator includes:

a puncture component including a handle housing, a puncture actuator movably arranged on the handle housing, and a force feedback mechanism arranged at a bottom of the handle housing, the force feedback mechanism and the puncture actuator being connected, the force feedback mechanism applying resistance to the puncture component based on puncture force feedback information, and the puncture actuator including a sliding component, wherein the sliding component includes a slip ring and a slide block connected to the slip ring, and the slip ring sleeves an outer side of the handle housing; and an attitude adjustment part;

wherein the puncture actuator further includes a puncture enabling component disposed on the sliding component, and a linear motion component disposed inside the handle housing, wherein the sliding component is slidably arranged on the handle housing and connected to the linear motion component, the puncture enabling component is electrically connected to a communication device, and the puncture enabling component feeds back a puncture enabling signal to an end of a robotic arm through the communication device.

19. A master manipulator of a robot, comprising:

a puncture component including a handle housing, a puncture actuator movably arranged on the handle housing, and a force feedback mechanism arranged at a bottom of the handle housing, the force feedback mechanism and the puncture actuator being connected, the force feedback mechanism applying resistance to the puncture component based on puncture force feedback information, the puncture component being a hollow columnar structure, and the puncture component rotating along a spindle of the hollow columnar structure; and an attitude adjustment part.

* * * * *